(12) United States Patent
Thulé

(10) Patent No.: US 7,790,690 B2
(45) Date of Patent: Sep. 7, 2010

(54) GLUCOSE SENSITIVE REGULATOR OF INSULIN TRANSCRIPTION

(75) Inventor: Peter M. Thulé, Atlanta, GA (US)

(73) Assignee: U.S. Department of Veterans Affairs, Washington, DC (US)

( * ) Notice: Subject to any disclaimer, the term of this patent is extended or adjusted under 35 U.S.C. 154(b) by 2008 days.

(21) Appl. No.: 09/972,916

(22) Filed: Oct. 10, 2001

(65) Prior Publication Data

US 2002/0107198 A1 Aug. 8, 2002

Related U.S. Application Data

(60) Provisional application No. 60/239,113, filed on Oct. 11, 2000.

(51) Int. Cl.
*A61K 31/70* (2006.01)
(52) U.S. Cl. .................................................. 514/44
(58) Field of Classification Search .............. 435/320.1; 514/44
See application file for complete search history.

(56) References Cited

U.S. PATENT DOCUMENTS

| | | | |
|---|---|---|---|
| 3,655,516 A | 4/1972 | Roon et al. | |
| 4,071,413 A | 1/1978 | Takahashi et al. | |
| 4,331,762 A | 5/1982 | Nakajima et al. | |
| 4,599,311 A | 7/1986 | Kawasaki | |
| 4,608,335 A | 8/1986 | Fossati | |
| 4,623,625 A | 11/1986 | Scopes | |
| 4,735,897 A | 4/1988 | Vary et al. | |
| 4,812,400 A | 3/1989 | Steinman | |
| 5,218,091 A | 6/1993 | Kawasaki | |
| 5,304,473 A | 4/1994 | Belagaje et al. | |
| 5,334,507 A | 8/1994 | Soya et al. | |
| 5,446,024 A | 8/1995 | Builder et al. | |
| 5,514,386 A | 5/1996 | Domingues | |
| 5,545,618 A | 8/1996 | Buckley et al. | |
| 5,554,504 A | 9/1996 | Rutanen | |
| 5,597,700 A | 1/1997 | Konstantinov et al. | |
| 5,604,115 A | 2/1997 | Sladek et al. | |
| 5,712,103 A | 1/1998 | Leavitt et al. | |
| 5,739,169 A | 4/1998 | Ocain et al. | |
| 5,747,273 A | 5/1998 | Khosravi et al. | |
| 5,750,398 A | 5/1998 | Johnson et al. | |
| 5,849,485 A | 12/1998 | Sladek et al. | |
| 5,866,378 A | 2/1999 | Marquardt et al. | |
| 5,877,029 A | 3/1999 | Fuks et al. | |

(Continued)

FOREIGN PATENT DOCUMENTS

WO WO 98/20906 5/1998

OTHER PUBLICATIONS

Vaulont, S. et al. (J. Mol. Biol. 1989, vol. 209, pp. 205-219).*

(Continued)

*Primary Examiner*—J. E Angell
(74) *Attorney, Agent, or Firm*—Dinesh Agarwal, P.C.

(57) ABSTRACT

A glucose sensitive regulator of insulin transcription includes a glucose response element (GIRE) of a liver-pyruvate (L-PK) gent promoter, and an insulin-sensitive element of an insulin-like growth factor binding protein-1 (IGFBP-1) basal promoter. The transcriptional activity of the regulator is stimulated by glucose and inhibited by insulin.

20 Claims, 21 Drawing Sheets

U.S. PATENT DOCUMENTS

| | | | |
|---|---|---|---|
| 5,888,705 | A | 3/1999 | Rubin et al. |
| 5,891,722 | A | 4/1999 | Fuks et al. |
| 5,914,449 | A | 6/1999 | Murase et al. |
| 5,968,758 | A | 10/1999 | Fuks et al. |
| 6,025,196 | A | 2/2000 | Sladek et al. |
| 6,113,903 | A | 9/2000 | Albertini et al. |
| 6,114,306 | A | 9/2000 | De Medicis et al. |
| 2001/0007656 | A1 | 7/2001 | Bosch et al. |

OTHER PUBLICATIONS

Goswami, R. et al. (Endocrinology 1994, vol. 134, pp. 736-743).*
Genes & Genomes (Sanger and Berg, 1991), p. 462.*
Thulé, P. M. and Liu, J., *Glucose Regulated Hepatic Production of Human Insulin Ameliorates Hyperglycemia in Streptozotocin Treated Rats*. Presented at the American Society of Gene Therapy, 2$^{nd}$ Annual Meeting, Washington, D.C., Jun. 9-13, 1999, 1 page.
Thulé, P. M. and Liu, J., *Glucose-regulated human insulin production from hepatocytes in STZ-treated rats: a model of insulin gene therapy*. Presented at 59$^{th}$ Annual Meeting, American Diabetes Association, Jun. 19-22, 1999, published as Supplement to Diabetes, May 1999, 1 page.
Thulé, P. M. and Liu, J., *Regulated Production of Insulin from Hepatocytes in Primary Cultures*. Oral Presentation, American Diabetes Associated, 58$^{th}$ Annual Scientific Sessions, Chicago, Illinois, Jun. 1998, 1 page.
Thulé, P. M. *Glucose-Regulated Human Insulin Production from Hepatocytes in STZ-Treated Rats: A Model of Insulin Gene Therapy*. Diabetes 48 Supplement (1): A0246, Jun. 19-22, 1999.
Thulé, P. M. and Liu, J., *Regulated Production of Insulin from Hepatocytes in Primary Cultures*, Diabetes 47 Supplement (1): A0263, Jun. 13-16, 1998.
Thulé, P. M., Liu, J. and Phillips, L. S. *Glucose Regulated Production of Human Insulin in Rat Hepatocytes*, submitted to Journal of Biological Chemistry (Jan. 1999), but rejected.
Thulé, P. M., Liu, J. and Phillips L. S. *Glucose regulated production of human insulin in rat Hepatocytes*, Gene Therapy 2000, 7(3):205-214.
Thulé, P. M. and Liu, J., *Regulated hepatic insulin gene therapy of STZ-diabetic rats*, Gene Therapy 2000, 7:1744-1752.
Eisenbarth GS. Type I diabetes mellitus: *A chronic autoimmune disease*. N Engl J Med 1986; 314:1360-1368.
Falqui L, Martinenghi S, Severini GM, et al. *Reversal of diabetes in mice by implantation of human fibroblasts genetically engineered to release mature human insulin*. Human Gene Therapy 1999; 10:1753-1762.
Muzzin P, Eisensmith RC, Copeland KC, Woo SLC. *Hepatic insulin gene expression as treatment for Type 1 diabetes mellitus in rats*. Mol Endo 1997; 11(6):833-837.
Gros L, Riu E, Montoliu L, Ontiveros M, Lebrigand L, Bosch F. *Insulin production by engineered muscle cells*. Human Gene Therapy 1999; 10:1207-1217.
Short DK, Okada S, Yamauchi K, Pessin JE. *Adenovirus-mediated transfer of a modified human proinsulin gene reverses hyperglycemia in diabetic mice*. American Journal of Physiology 1998; 275:E748-E756.
Rivera VM, Wang W, Wardwell S, et al. *Regulation of protein secretion through controlled aggregation in the endoplasmic reticulum*. Science 2000, 287:826-830.
Selden RF, Skoskiewicz MJ, Russell PS, Goodman HM. *Regulation of insulin-gene expression*. N Engl J Med 1987; 317:1067-1076.
Kolodka TM, Finegold M, Moss L, Woo SLC. *Gene therapy for diabetes mellitus in rats by hepatic expression of insulin*. Proc Natl Acad Sci USA 1995; 92:3293-3297.
Tuch BE, Tabiin MT, Casamento FM, Simpson AM, Marshall GM. *Transplantation of genetically engineered insulin-producing Hepatocytes into immunoincompetent mice*. Transplantation Proceedings 1998; 30:473.
Valera A, Fillat C, Costa C, et al. *Regulated expression of human insulin in the liver of transgenic mice corrects diabetic alterations*. FASEB J 1994; 8(6):440-447.
Kaneda Y, Iwai K, Uchida T. *Introduction and expression of the human insulin gene in adult rat liver*. Journal of Biological Chemistry 1989; 264(21):12126-12129.
Yamaguchi M, Kuzume M, Matusumoto T, et al. *Insulin gene transfer compensates pancreatic β-cell function in diabetic rats*. Transplantation Proceedings 1998; 30:2913.
Sugiyama A, Hattori S, Tanaka S, et al. *Defective adenoassociated viral-mediated transfection of insulin gene by direct injection into liver parenchyma decreases blood glucose of diabetic mice*. Hormone and Metabolic Research 1997; 29(12):599-603.
Abai A, Hobart P, Barnhart KM. *Insulin Delivery with Plasmid DNA*. Human Gene Therapy 1999; 10:2637-2649.
Lu D, Tamemoto H, Shibata H, Saito I, Takeuchi T. *Regulatable production of insulin from primary-cultured hepatocytes: insulin production is up-regulated by glucagon and cAMP and down-regulated by insulin*. Gene Therapy 1998; 5(7):888-895.
Gros L, Montoliu L, Riu E, Lebrigand L, Bosch F. *Regulated production of mature insulin by non-b-cells*. Human Gene Therapy 1997; 8(18):2249-2259.
Wanke IE, Wong NC. *Specific problems facing gene therapy for insulin-dependent diabetes mellitus: glucose-regulated insulin secretion from hepatocytes*. Proceeding of the Western Pharmacology Society 1997; 40:131-133.
Simpson AM, Marshall GM, Tuch BE, et al. *Gene therapy of diabetes: glucose-stimulated insulin secretion in a human hepatoma cell line (HEP G2ins/g)*. Gene Therapy 1997; 4:1202-1215.
Powell DR, Suwanichkul A, Cubbage M, Lee PDK. *Regulation of insulin-like growth factor binding protein-1 (IGFBP-1) protein levels, mRNA levels and promoter activity by insulin (IN) and IGF-1 in HepG2*. Endo Society 1990:280A.
Powel DR, Suwanichkul A, Cubbage ML, DePaolis LA, Snuggs MB, Lee PDK. *Insulin inhibits transcription of the human gene for insulin-like growth factor-binding protein-1*. Journal of Biological Chemistry 1991; 266:18868-18876.
Powell DR, Suwanichkul A. *HNF1 activates transcription of the human gene for insulin-like growth factor binding protein-1*. DNA and Cell Biology 1993; 12:283-289.
Suwanichkul A, Cubbage ML, Powell DR. The promoter of the human gene for insulin-like growth factor binding protein-1. *Basal promoter activity in HEP G2 cells depends upon liver factor B1*. Journal of Biological Chemistry 1990; 265:21185-21193.
Suwanichkul A, DePaolis LA, Lee PDK, Powell DR. *Identification of a promoter element which participates in cAMP-stimulated expression of human insulin-like growth factor-binding protein-1*. Journal of Biological Chemistry 1993; 268:9730-9736.
Suwanichkul A, Morris SL, Powell DR. *Identification of an insulin-responsive element in the promoter of the human gene for insulin-like growth factor binding protein-1*. Journal of Biological Chemistry 1993; 268:17063-17068.
Suwanichkul A, Allander SV, Morris SL, Powell DR. *Glucocorticoids and insulin regulate expression of the human gene for insulin-like growth factor-binding protein-1 through proximal promoter elements*. Journal of Biological Chemistry 1994; 269:30835-30841.
Hughes SD, Johnson JH, Quaade C, Newgard CB. *Engineering of glucose-stimulated insulin secretion and biosynthesis in non-islet cells*. 1992; 89:688-692.
Rencurel F, Waever G, Antoine B, et al. *Requirement of glucose metabolism for regulation of glucose transporter type 2 (GLUT 2) gene expression in liver*. Biochemical Journal 1996; 314:903-909.
Villafuerte BC, Goldstein S, Murphy LJ, Phillips LS. *Nutrition and Somatomedin XXV. Regulation of insulin-like growth factor binding protein-1 in primary cultures of normal rat hepatocytes*. Diabetes 1991; 40:837-841.
Ooi GT, Tseng LY-H, Tran MQ, Rechler MM. *Insulin rapidly decreases insulin-like growth factor-binding protein-1 gene transcription in streptozotocin-diabetic rats*. Molecular Endocrinology 1992; 6:2219-2228.
Pao C-I, Farmer PK, Begovic S, Goldstein S, Wu G-J, Phillips LS. *Expression of hepatic insulin-like growth factor-I and insulin-like growth factor-binding protein-1 genes is transcriptionally regulated in streptozotocin-diabetic rats*. Molecular Endocrinology 1992; 6:969-977.

Suh D-S, Zhou Y, Ooi GT, Rechler MM. *Dexamethasone stimulation of rat insulin-like growth factor binding protein-1 (IGFBP-1) promoter activity involves the interaction of multiple transcription factors*. Progress in Growth Factor Research 1995; 6:131-140.

Cuif M-H, Cognet M, Boquet D, Tremp G, Kahn A, Vaulont S. *Elements responsible for hormonal control and tissue specificity of L-type pyruvate kinase gene expression in transgenic mice*. Molecular and Cellular Biology 1992; 12:4852-4861.

Cognet M, Lone YC, Vaulont S, Kahn A, Marie J. *Structure of the rat L-type pyruvate kinase gene*. J Mol Biol 1987; 196:11-25.

Bergot M-O, Diaz-Guerra M-JM, Puzenat N, Raymondjean M, Kahn A. *Cis-regulation of the L-type pyruvate kinase gene promoter by glucose, insulin and cyclic AMP*. Nucleic Acids Research 1992; 20(8):1871-1878.

Vaulont S, Munnich A, Decauz J-F, Kahn A. *Transcriptional and post-transcriptional regulation of L-type pyruvate kinase gene expression in rat liver*. Journal of Biological Chemistry 1986; 261:7621-7625.

Goswami R, Lacson R, Unterman T. *Identification of insulin and glucocorticoid response sequences in the rat IGF binding protein-1 (IGFBP-1) promoter*. Endocrine Society 1993; 1915B:529.

Shu D-S, Ooi GT, Lesniak MAS. *Inhibition of IGFBP-1 gene expression by insulin and stimulation by dexamethasone, cyclic amp, and phorbol esters are mediated by different cis-acting elements in the rat IGFBP-1 promoter*. Endocrine Society 1993; 1916B:529.

Smeekens SP, Chan SJ, Steiner DF. *The biosynthesis and processing of neuroendocrine peptides: identification of proprotein convertases involved in intravesicular processing*. Progress in Brain Research 1992; 92:235-246.

Groskreutz DJ, Sliwkowski MX, Gorman CM. *Genetically engineered proinsulin constitutively processed and secreted as mature, active insulin*. Journal of Biological Chemistry 1994; 269(8):6241-6245.

Steiner DF, Smeekens SP, Ohagi S, Chan SJ. *The New Enzymology of Precursor Processing Endoproteases*. Journal of Biological Chemistry 1992; 267:23435-23438.

Simonson GD, Groskreutz DJ, Gorman CM, MacDonald MJ. *Synthesis and processing of genetically modified human proinsulin by rat myoblast primary cultures*. Human Gene Therapy 1996; 7:71-78.

Unger RH, Foster DW, Chapter 21. In: Wilson JD, Foster DW, Kronenberg HM, Williams RH, eds. *Williams Textbook of Endocrinology*. vol. 9th. Philadelphia, London, Toronto, Montreal, Sydney: W.B Saunders Co., 1998:973-1059.

Robertson DG, Marino EM, Thule PM, Seneviratne CK, Murphy LJ. *Insulin and glucocorticoids regulate IGFBP-1 expression via a common promoter region*. Biochemical Biophysical Research Communications 1994; 200(1):226-232.

Goswami R, Lacson R, Yang E, Sam R, Unterman T. *Functional analysis of glucocorticoid and insulin response sequences in the rat insulin-like growth factor-binding protein-1 promoter*. Endocrinology 1994; 134:736-743.

Suh DS, Ooi GT, Rechler MM. *Identification of cis -elements mediating the stimulation of rat insulin-like growth factor-binding protein-1 promoter activity by dexamethasone, cyclic adenosine 3',5'-monophosphate, and phorbol esters, and inhibition by insulin*. Molecular Endocrinology 1994; 8:794-805.

Goldstein S, Sertich G, Levan KR, Phillips LS. *Nutrition and somatomedin. XIX. Molecular regulation of insulin-like growth factor-I in streptozotocin-diabetic rats*. Molecular Endocrinology 1988; 2:1093-1100.

Minematsu S, Watanabe M, Tsuchiya N, Amagaya S. *Diurnal variations in blood chemical items in Sprague-Dawley rats*. Experimental Animals 1995; 44:223-232.

Haughton CL, Dillehay DL, Phillips LS. *Insulin replacement therapy for the rat model of streptozotocin-induced diabetes mellitus*. Laboratory Animal Science 1999; 49:639-644.

Koopmans SJ, Sips HCM, Krans HMJ, Radder JK. *Pulsatile intravenous insulin replacement in streptozotocin-diabetic rats is more efficient than continuous delivery:effects on glycaemic control, insulin-mediated glucose metabolism and lipolysis*. Diabetologia 1996; 39:391-400.

Wang RN, Bouwens L, Kloeppel G. *Beta-cell proliferation in normal and streptozotocin-treated newborn rats: site, dynamics and capacity*. Diabetologia 1994; 37:1088-1096.

Like AA, Guberski DL, Butler L. *Influence of Environmental Viral Agents on Frequency and Tempo of Diabetes Mellitus in BB/Wor Rats*. Diabetes 1991; 40:259-262.

Seglen PO. Preparation of rat liver cells. III. *Enzymatic requirements for tissue dispersion*. Exp Cell Res 1973; 82:391-398.

Ginot F, Decaux J-F, Cognet M, et al. *Transfection of hepatic genes into adult rat hepatocytes in primary culture and their tissue-specific expression*. Eur J Biochem 1989; 180:289-294.

Baker A, Saltik M, Lehrmann H, et al. *Polyethylenimine (PEI) is a simple, inexpensive and effective reagent for condensing and linking plasmid DNA to adenovirus for gene delivery*. Gene Therapy 1997; 4:773-782.

Marriott D, Gillece-Castro B, Gorman CM. *Prohormone convertase-1 will process prorelaxin, a member of the insulin family of hormones*. Molecular Endocrinology 1992: 6:1441-1450.

Mittereder N, March KL, Trapnell BC. *Evaluation of the concentration and bioactivity of adenovirus vectors for gene therapy*. Journal of Virology 1996; 70:7498-7509.

Alam T. *Reduction in diabetic hyperglycemia by glucose-regulated insulin release from transduced hepatocytes*. University of Wisconsin Department of Surgery (Undated). (4 pages) Web site: http://www.surgery.wisc.edu/research/txlab_ta-rotrf.html.

Bloomgarden, Z. *New approaches to insulin treatment and glucose monitoring*. (American Diabetes Association Annual Meeting, 1999. Diabetes care 22(12):2078. (13 pages).

Ferber S, Halkin A, Cohen H, Ber I, Einav Y, Goldberg I, Barshack I, Seijffers R, Kopolovic J, Kaiser N, Karasik A. *Pancreatic and duodenal homeobox gene 1 induces expression of insulin genes in liver and ameliorates streptozotocin-induced hyperglycemia*. Nature medicine May 2000; 6(5):568-572.

Institute of Human Gene Therapy, University of Pennsylvania Health System. *Prospects in gene therapy*. Mar. 11, 1999. (4 pages) Web site: http://med.upenn.edu/ihgt/info/prospcts.html.

Leibiger B, Moede T, Schwarz T, Brown G.R., Köhler M, Leibiger I.B., Berggren, P-O. *Short-term regulation of insulin gene transcription by glucose*. Proceedings of the National Academy of Sciences 1998; 95(16):9307-9312.

National Institutes for Diabetes & Digestive & Kidney Diseases. *Diabetes statistics*. National Diabetes Information Clearinghouse, NIH Publication No. 99-3892, Mar. 1999. (11 pages) Web site: http://www.niddk.nih.gov/health/diabetes/pubs/dmsats/dmstats.htm#what.

Osborne W, Barry, S. *Glucose-regulated insulin expression in diabetic rats*. Molecular therapy May 2000; 1(5):S27-S31. (2 pages).

Rajan, A. *An update on islet cell replacement*. American Diabetes Association's 59th Scientific Session, Day 4, Jun. 22, 1999. (6 pages) Web site: http://www.islet.org/forum/messages/8637.htm.

Simpson AM, Tuch BE, Swan MT, Tu J, Marshall GM. *Functional expression of the human insulin gene in a human hepatoma-cell line (hep g2)*. Gene therapy 1995; 2(3):223-231.

Tomita N, Oghihara T, Kondo T, Kanyeda Y. *A novel gene-transfer technique mediated by HVJ (Sendai virus), nuclear-protein and liposomes*. Cancer detection and prevention 1994; 18(6):485-491.

Woo S, Lernmark A. *Gene therapy approaches for diabetes and its complications: summary and recommendations*. NIDDK Conference Reports and Archives, Nov. 8-9, 1999. (5 pages) Web site: http://www.niddk.nij.gov/fund/reports/gene_therapy_summ.htm.

Hasegawa J., Osatomi K., Wu R-F., and Uyeda K., *A Novel Factor Binding to the Glucose Response Elements of Liver Pyruvate Kinase and Fatty Acid Synthase Genes*. Journal of Biological Chemistry 1999; 274(2):1100-1107.

Lou D-Q., Tannour M., Selig L., Thomas D., Kahn A., and Vasseur-Cognet M., *Chicken Ovalbumin Upstream Promoter-Transcription Factor II, a New Partner of the Glucose Response Element of the L-type Pyruvate Kinase Gene, Acts as an Inhibitor of the Glucose Response*. Journal of Biological Chemistry 1999; 274(40):28385-28394.

Powell D.R., Allander S.V., Scheimann A.O., Wasserman R.M., Durham S.K., and Suwanichkul A., *Multiple Proteins Bind the Insu-*

*lin Response Element in the Human IGFBP-1 Promoter*. Progress in Growth Factor Research 1995; 6(2-4):93-101.

"A Model of Insulin Gene Therapy", Emory University, Medical Grand Rounds, Apr. 14, 1998. PowerPoint file: Emory Grand Rounds Apr. 21, 1998 (48 printed slides).

Thulé PM, Liu J. Regulated production of insulin from hepatocytes in primary culture. Diabetes 47 (Suppl 1), American Diabetes Assoc., 58$^{th}$ Annual Meeting, Jun. 13-16, 1998. Word file: ADA LSPdone Jan. 2, 1998 (1 page). PowerPoint file: ADA Talk Jun. 1998 (30 printed slides).

Thulé PM, Liu J. Glucose-regulated human insulin production from hepatocytes in STZ-treated rats: a model of insulin gene therapy. Diabetes 48 (Suppl 1), American Diabetes Assoc., 59$^{th}$ Annual Meeting, Jun. 19-22, 1999. Word file: ADA Abstract Jun. 1999 (1 page). PowerPoint file: ADA Jun. 6, 1999(17 printed slides).

Thulé PM, Liu J. Glucose regulated hepatic production of human insulin ameliorates hyperglycemia in streptozotocin treated rats. American Society of Gene Therapy, 2$^{nd}$ Annual Meeting, Jun. 9-13, 1999. Word file: Abstract Mar. 1, 1999a(1 page). Press Release VA Researchers Develop Potential Gene Therapy for Diabetes, Jun. 13, 1999 (2 pages). PowerPoint file: Gene Therapy Abs. Jun. 1999 May 24 (24 printed slides).

"Progress Toward Insulin Gene Therapy", Georgia Diabetes Research Consortium, Atlanta, GA, Sep. 22, 1999. PowerPoint file: GA Diabetes Consortium Sep. 23, 1999 (50 printed slides).

"Gene Therapy into the Future", Columbus General Hospital, Medical Grand Rounds, Columbus Georgia, May 16, 2000. Word file: Day at Columbus (1 page letter). PowerPoint file: Columbus Grand Rounds May 16, 2000 (82 printed slides).

Thulé PM, Liu J. Expression-level dependent human proinsulin processing by furin in primary hepatocytes. Molecular Therapy 1(5), supp. 1, Apr./May 2000 (Abstract No. 816—1 page). Word file: Poster29May ASGT Jun. 2000 (13 pages). PowerPoint files: Figs ASGT Poster & figure1 (4 printed slides).

"Advances in Insulin Gene Therapy", Crawford W. Long Hospital, Atlanta, GA, Medical Grand Rounds, Mar. 30, 2001. Powerpoint file: CWL Grand Rounds Fri Mar. 30, 2001 (67 printed slides).

Thulé PM, Martin, SA, Olson, DE, Porter, MH. 2001 Glucose and insulin responsive hepatic insulin gene therapy in spontaneously diabetic BB Wor rats. Molecular Therapy 3(5), 2/2, S94, May 2001 (Abstract No. 268-1 page). Word file: ThulePoster ASGT Figs Jun. 2001 (14 pages).

Porter, MH, Martin, SA, Olson, DE, Thulé PM. Intrahepatic insulin production modifies intermediary carbohydrate metabolism in primary cultured hepatocytes. Molecular Therapy 3(5). 2/2. S232, May 2001 (Abstract No. 661—1 page). Word files: Porter Martin Olson Thule (1 page) (text of abstract). ASGTPorter with Figs Jun. 2001 (10 pages) has been replaced with ASGT Porter, Paveglio, Olson &Thule May 22 (10 pages).

Kozlowski M, Rubin J, Thulé PM. Delivery of regulatable insulin secretion system via AAV into hepatocytes in vitro. Molecular Therapy 3(5), 2/2, S396, May 2001 (Abstract No. 1129—2 pages). Word files: Kozlowski Rubin Thule01 (abstract text—1 page). Kozlowski May 22, 2001 (12 pages). PowerPoint file: Fig 1-7 pic1 (7 printed slides).

"Hepative Insulin Gene Therapy", Annual Meeting, Richmond, VA Chapter, Juvenile Diabetes Research Foundation, Jun. 16, 2001. Powerpoint file: JDRF19Jun01 (61 printed slides).

Unterman TG, Lacson RG, McGary E, Whalen C, Purple C, Goswami RG. Cloning of the rat insulin-like growth factor binding protein-1 gene and analysis of its 5' promoter region. *Biochemical Biophysical Research Communication* 1992;185(3):993-999.

Inoue H, Noguchi T, Tanaka T. Complete amino acid sequence of rat L-type pyruvate kinase deduced from the cDNA sequence. *European Journal of Biochemistry* 1986;154(2):465-9.

Yamada K, Tanaka T, Noguchi T. Members of the nuclear factor 1 family and hepatocyte nuclear factor 4 bind to overlapping sequences of the L-11 element of the rat pyruvate kinase L gene promoter and regulate its expression. *Biochem J* 1997;324:917-925.

Unterman TG, Fareeduddin A, Harris MA, Goswami RG, Porcella A, Costa RH, et al. Hepatocyte nuclear factor-3 (HNF-3) binds to the insulin response sequence in the IGF binding protein-1 (IGFBP-1) promoter and enhances promoter function. *Biochemical Biophysical Research Communication* 1994:203:1835-1841.

Bergot MO, Diaz-Guerra MJM, Puzenat N, Raymondjean M and Kahn A. *Cis*-regulation of the L-type pyruvate kinase gene promoter by glucose, insulin and cyclic AMP. *Nucleic Acids Research*, Vo. 20, No. 8, pp. 1871-1878 (1992).

Mitanchez D, Chen R, Massias JF, Porteu A, Mignon A, Bertagna X and Kahn A. Regulated expression of mature human insulin in the liver of transgenic mice. FEBS Letters 421 (1998) pp. 285-289.

Mitanchez D, Doiron B, Chen R and Kahn A. Glucose-Stimulated Genes and Prospects of Gene Therapy for Type I Diabetes. Endocrine Reviews (1997) vol. 18, No. 4, pp. 520-540.

Lee HC, Kim SJ, Kim KS, Shim HC and Yoo JW. Remission in models of type 1 diabetes by gene therapy using a single-chain insulin analogue. Nature, vol. 408, Nov. 23, 2000, pp. 483-488. Rectracted Nature, vol. 458, Apr. 2, 2009 (1 page).

Chen R, Meseck ML and Woo SLC. Auto-regulated Hepatic Insulin Gene Expression in Type 1 Diabetic Rats. Molecular Therapy vol. 3, No. 4, Apr. 2001, pp. 584-590.

\* cited by examiner

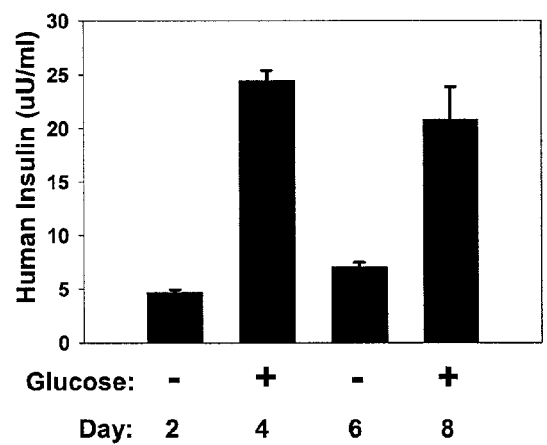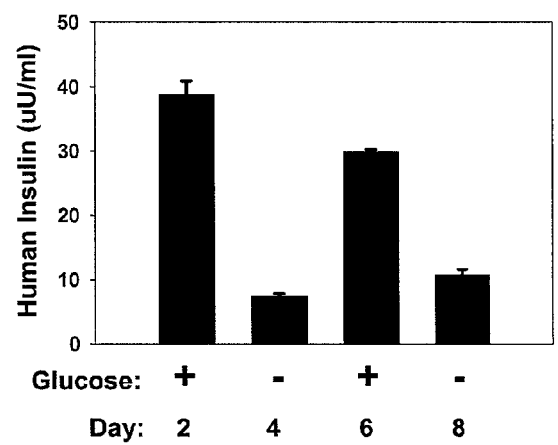
FIG. 13A  FIG. 13B

SEQUENCE LISTING

<160> NUMBER OF SEQ ID NOS: 14

<210> SEQ ID NO 1
<211> LENGTH: 51
<212> TYPE: DNA
<213> ORGANISM: Rattus norvegicus
<220> FEATURE:

<400> SEQUENCE: 1
catgggcgca cggggcactc ccgtggttcc tggactctgg cccccagtgt a       51

<210> SEQ ID NO 2
<211> LENGTH: 219
<212> TYPE: DNA
<213> ORGANISM: Rattus norvegicus
<220> FEATURE:

<400> SEQUENCE: 2
tcacaagcaa aacaaactta ttttgaacac ggggatccta gcacgctgcc ctgacaatca       60
ttaacccgtg ctgccgagcc agcccttcat aaggccctgg gtatggccag ccagcatggt      120
ccactgcccg ccgagacaca aacccagcga gcattgaaca ctgcacacgg ccatctgccc      180
agagagctgt gaccaccact tccgctacta gctagccgc                             219

<210> SEQ ID NO 3
<211> LENGTH: 270
<212> TYPE: DNA
<213> ORGANISM: Artificial Sequence
<220> FEATURE:
<223> OTHER INFORMATION: Synthesized

<400> SEQUENCE: 3
catgggcgca cggggcactc ccgtggttcc tggactctgg cccccagtgt atcacaagca       60
aaacaaactt attttgaaca cggggatcct agcacgctgc cctgacaatc attaacccgt      120
gctgccgagc cagcccttca taaggccctg ggtatggcca gccagcatgg tccactgccc      180
gccgagacac aaacccagcg agcattgaac actgcacacg gccatctgcc cagagagctg      240
tgaccaccac ttccgctact agctagccgc                                       270

<210> SEQ ID NO 4
<211> LENGTH: 321

<212> TYPE: DNA
<213> ORGANISM: Artificial Sequence
<220> FEATURE:
<223> OTHER INFORMATION: Synthesized

<400> SEQUENCE: 4

| tacactgggg gccagagtcc aggaaccacg ggagtgcccc gtgcgcccat gtacactggg | 60 |
| ggccagagtc caggaaccac gggagtgccc cgtgcgccca tgtcacaagc aaaacaaact | 120 |
| tattttgaac acggggatcc tagcacgctg ccctgacaat cattaacccg tgctgccgag | 180 |
| ccagcccttc ataaggccct gggtatggcc agccagcatg gtccactgcc cgccgagaca | 240 |
| caaacccagc gagcattgaa cactgcacac ggccatctgc cagagagct gtgaccacca | 300 |
| cttccgctac tagctagccg c | 321 |

<210> SEQ ID NO 5
<211> LENGTH: 372
<212> TYPE: DNA
<213> ORGANISM: Artificial Sequence
<220> FEATURE:
<223> OTHER INFORMATION: Synthesized

<400> SEQUENCE: 5

| tacactgggg gccagagtcc aggaaccacg ggagtgcccc gtgcgcccat gtacactggg | 60 |
| ggccagagtc caggaaccac gggagtgccc cgtgcgccca tgtacactgg gggccagagt | 120 |
| ccaggaacca cgggagtgcc ccgtgcgccc atgtcacaag caaaacaaac ttattttgaa | 180 |
| cacggggatc ctagcacgct gccctgacaa tcattaaccc gtgctgccga gccagccctt | 240 |
| cataaggccc tgggtatggc cagccagcat ggtccactgc cgccgagac acaaacccag | 300 |
| cgagcattga acactgcaca cggccatctg cccagagagc tgtgaccacc acttccgcta | 360 |
| ctagctagcc gc | 372 |

<210> SEQ ID NO 6
<211> LENGTH: 423
<212> TYPE: DNA
<213> ORGANISM: Artificial Sequence
<220> FEATURE:
<223> OTHER INFORMATION: Synthesized

<400> SEQUENCE: 6

| catgggcgca cggggcactc ccgtggttcc tggactctgg cccccagtgt acatgggcgc | 60 |
| acggggcact cccgtggttc ctggactctg gcccccagtg tacatgggcg cacggggcac | 120 |
| tcccgtggtt cctggactct ggcccccagt gtacatgggc gcacggggca ctcccgtggt | 180 |
| tcctggactc tggcccccag tgtatcacaa gcaaaacaaa cttattttga acacggggat | 240 |
| cctagcacgc tgccctgaca atcattaacc cgtgctgccg agccagccct tcataaggcc | 300 |
| ctgggtatgg ccagccagca tggtccactg cccgccgaga cacaaaccca gcgagcattg | 360 |
| aacactgcac acggccatct gcccagagag ctgtgaccac cacttccgct actagctagc | 420 |
| cgc | 423 |

<210> SEQ ID NO 7
<211> LENGTH: 34
<212> TYPE: DNA
<213> ORGANISM: Artificial Sequence
<220> FEATURE:
<223> OTHER INFORMATION: Synthesized

<400> SEQUENCE: 7

```
gcgacgcgtt cccttaggta ttccttgagt tcgg                                34
```

<210> SEQ ID NO 8
<211> LENGTH: 34
<212> TYPE: DNA
<213> ORGANISM: Artificial Sequence
<220> FEATURE:
<223> OTHER INFORMATION: Synthesized

<400> SEQUENCE: 8

```
gcggctagct agtagcggaa gtggtggttc acag                                34
```

<210> SEQ ID NO 9
<211> LENGTH: 48
<212> TYPE: DNA
<213> ORGANISM: Artificial Sequence
<220> FEATURE:
<223> OTHER INFORMATION: Synthesized

<400> SEQUENCE: 9

```
gggcgcacgg ggcactcccg tggttcctgg actctggccc ccagtgta                 48
```

<210> SEQ ID NO 10
<211> LENGTH: 51
<212> TYPE: DNA
<213> ORGANISM: Artificial Sequence
<220> FEATURE:
<223> OTHER INFORMATION: Synthesized

<400> SEQUENCE: 10

```
atgtacactg ggggccagag tccaggaacc acgggagtgc cccgtgcgcc c             51
```

<210> SEQ ID NO 11
<211> LENGTH: 21
<212> TYPE: DNA
<213> ORGANISM: Artificial Sequence
<220> FEATURE:
<223> OTHER INFORMATION: Synthesized

<400> SEQUENCE: 11

```
accatggccc tgtggatgcg c                                              21
```

<210> SEQ ID NO 12
<211> LENGTH: 21
<212> TYPE: DNA
<213> ORGANISM: Artificial Sequence
<220> FEATURE:
<223> OTHER INFORMATION: Synthesized

<400> SEQUENCE: 12

```
ctagttgcag tagttctcca g                                              21
```

<210> SEQ ID NO 13
<211> LENGTH: 19
<212> TYPE: DNA
<213> ORGANISM: Artificial Sequence
<220> FEATURE:
<223> OTHER INFORMATION: Synthesized

<400> SEQUENCE: 13

```
ctggtcatca atgggaaac                                                 19
```

<210> SEQ ID NO 14
<211> LENGTH: 20
<212> TYPE: DNA
<213> ORGANISM: Artificial Sequence

```
<220> FEATURE:
<223> OTHER INFORMATION: Synthesized

<400> SEQUENCE: 14
caaagttgtc atggatgacc                                                    20
```

GLUCOSE SENSITIVE REGULATOR OF INSULIN TRANSCRIPTION

CROSS-REFERENCE TO RELATED APPLICATIONS

The present application claims priority on prior U.S. Provisional Application Ser. No. 60/239,113, filed Oct. 11, 2000, and which is incorporated herein in its entirety by reference.

REFERENCE TO SEQUENCE LISTING

The present application incorporates by reference a file named: US 1292-01 Replacement Sequence Listing 4-21-04, including SEQ ID NO.: 1, SEQ ID NO.: 2, SEQ ID NO.: 3, SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, and SEQ ID NO.: 14 provided herewith on a diskette, created on Apr. 21, 2004 and containing 4,364 bytes. The information recorded on the diskette is identical to the written sequence listing provided herein.

BACKGROUND OF THE INVENTION

Type 1 diabetes mellitus (DM) is usually precipitated by autoimmune destruction of pancreatic β-cells, leading to insufficient insulin production (Reference 1). Since clinical symptoms are caused by diminished production of a single protein, diabetes is a natural candidate for treatment by gene therapy. The basic components of insulin gene therapy are widely available. Functional insulin genes can be transferred to multiple tissues (References 2-4), and the capacity of non-β-cells to secrete biologically active transgenic insulin in sufficient quantities to affect metabolism is well established (References 2-6). Multiple investigators have demonstrated functional insulin gene transfer both in vitro, and in vivo (References 2 and 7-8). However, attempts to regulate transgenic insulin production have proven inadequate (References 9-10). Consequently, in a variety of insulin gene transfer protocols secretion of transgenic insulin has been either insufficient to normalize blood glucose (References 2-5 and 10), has affected glycemia only moderately, or for short periods of time (References 4, 5 and 10-14), or has produced lethal hypoglycemia (References 2-3 and 8). Thus, for insulin gene therapy to be effective, it is widely accepted that insulin production must be regulated.

The critical importance of regulated transgenic insulin production was underscored by the work of Muzzin, et al. They successfully induced insulin production from the livers of STZ-treated rats by administering a retrovirus containing an insulin transgene (Reference 3). Transgenic insulin secretion was sufficient to prevent diabetic ketoacidosis, while permitting the animals to gain weight. Moreover, they avoided lethal hypoglycemia in a subset of animals by limiting vector dosage. However, reductions in vector sufficient to enable survival with prolonged fasting produced hyperglycemia when the animals were fed, presumably because transgenic insulin production could not increase to meet expanded demand (Reference 3). Others have demonstrated transgenic insulin secretion that is regulated by cAMP, glucocorticoids, insulin, or glucose by utilizing metabolically sensitive promoters in hepatocytes or hepatoma cells, and Simpson et al have demonstrated glucose responsiveness in insulin expressing HepG2 cells (References 15-18). However, transfer of these regulatory mechanisms to in vivo models has been difficult (Reference 9). We have overcome these limitations, and have developed a glucose and insulin sensitive promoter capable of appropriately coupling metabolic requirements for insulin, with insulin production from the liver of a diabetic animal.

OBJECTS AND SUMMARY OF THE INVENTION

An object of the present invention is to provide a glucose sensitive regulator of insulin transcription that regulates the transcription of an insulin expression sequence that has been introduced into liver-parenchymal cells (hepatocytes), or well-differentiated hepatoma cell lines.

Another object of the present invention is to provide a glucose sensitive regulator of insulin transcription wherein transcription of an insulin expression sequence is stimulated by exposure of these hepatocytes, either in vitro or in vivo, to glucose, but not other carbohydrates, such as lactate.

Yet another object of the present invention is to provide a glucose sensitive regulator of insulin transcription wherein transcription of an insulin expression sequence that is stimulated by glucose is inhibited by exposure of these hepatocytes to glucagon, and possibly other stimulators of cyclic-adenosine mono-phosphate within hepatocytes.

Still yet another object of the present invention is to provide a glucose sensitive regulator of insulin transcription wherein transcription is stimulated by exposure of cells to glucocorticoids.

An additional object of the present invention is to provide a glucose sensitive regulator of insulin transcription wherein the transcription is inhibited, either in vitro or in vivo, by exposure of hepatocytes to stimulators of the insulin receptor, including, but not limited to insulin from beef, pigs, humans, and rats, and probably including non-protein insulinomimetics.

Yet an additional object of the present invention is to provide a glucose sensitive regulator of insulin transcription wherein the combination of the aforementioned effects provides sufficient coupling between the actual metabolic requirement for insulin-action in, and the production of insulin-action as to maintain near euglycemia in diabetic animals, whether they are enduring a short (24-hours or less) fast, are subjected to large carbohydrate loads (i.e., a glucose-tolerance test), or are feeding ad libitum.

Still yet an additional object of the present invention is to provide a glucose sensitive regulator of insulin transcription which when coupled to an insulin expression sequence, provides sufficient regulation of insulin production to inhibit pathologic ketogenesis and the development of diabetic ketoacidosis in diabetic animals, and that this capacity is believed to be reproducable in humans.

Still yet an additional object of the present invention is to provide a glucose sensitive regulator of insulin transcription wherein the sum effect of glycemic control in animals, and by inference, people, treated with an insulin gene controlled by the invention is an inhibition of the processes leading to long-term complications in subjects with diabetes mellitus. Such complications include, but are not limited to, microvascular disease, macrovascular disease, serum lipid abnormalities, neuropathies, myopathies, and coagulopathies.

Another object of the present invention is to provide a glucose sensitive regulator of insulin transcription wherein the transcription of a transgene by the invention is minimal in non-hepatocyte, or non-hepatoma, or poorly-differentiated hepatoma cell lines, with the possible exception of certain kidney or small bowel, or endometrial cells.

Yet another object of the present invention is to provide a glucose sensitive regulator of insulin transcription wherein intracellular production of insulin within hepatocytes, mediated via the invention, may exert effects separate and distinguishable from those produced by secreted insulin. These effects may include the inhibition of cellular protein-degradation machinery, and either inhibitory or stimulatory effects on the actions of intracellular hormone receptors of the glucocorticoid, Vitamin D, thyroid-hormone, estrogen, progesterone, and androgen receptor class.

Still yet another object of the present invention is to provide a glucose sensitive regulator of insulin transcription wherein hepatic insulin production is believed to be capable of reducing protein catabolism during short term fasting, and may reduce protein catabolism in other catabolic conditions.

In summary, the present invention provides a hepatocyte specific promoter/regulator/transgene whose transcriptional activity is stimulated by glucose and inhibited by insulin. Application of this promoter in hepatocytes produces insulin transgene expression that is stimulated by exposure to glucose, and inhibited by exposure of cells to insulin. Glucocorticoids stimulate promoter activity independently of, and synergistically to glucose, while glucagon interferes with glucose stimulation. Glucose- and insulin-sensitive promoters were constructed by inserting glucose-responsive elements (GIRE's) from the rat L-pyruvate kinase (L-PK) gene into the insulin-sensitive, liver specific, rat insulin-like growth factor binding protein-1 (IGFBP-1) promoter. Glucose (5 to 25 mM) stimulated, and insulin ($10^{-10}$ to $10^{-7}$M) inhibited, reporter gene expression driven by these promoters in primary cultured rat hepatocytes. The capacity of transfected hepatocytes to secrete mature, biologically active insulin was demonstrated using a human proinsulin cDNA (2xfur), modified to allow protein processing by endogenous endopeptidase activity. Medium conditioned by insulin-producing hepatocytes contained greater than 300 µU/ml immunoreactive insulin, while denaturing SDS-PAGE of an anti-insulin immunoprecipitate revealed bands with the mobilities of insulin A, and B-chains. Biological activity of hepatocyte-produced insulin was demonstrated in a transfection assay, in which medium conditioned by insulin-producing hepatocytes exerted an effect similar to $10^{-7}$M insulin. The glucose and insulin sensitive promoter was then combined with the modified human pro-insulin cDNA to create a metabolically sensitive insulin transgene [(GIRE)$_3$BP-1 2xfur]. In both H4IIE hepatoma cells stably transfected with this construct, and normal rat hepatocytes, (GIRE)$_3$BP-1 2xfur mediated insulin secretion increased in response to stimulation by glucose. Moreover, a capacity to decrease insulin production in response to diminishing glucose exposure was also demonstrated.

To demonstrate application of the transgene of the invention, for the treatment of diabetes mellitus in vivo, a recombinant adenovirus vector, Ad/(GIRE)$_3$BP-1 2xfur, was administered to rats made diabetic with streptozotocin. The hepatic expression of transgenic insulin was verified by RT-PCR, and confirmed glucose responsive stimulation of transgenic insulin secretion in vivo by serum RIA. Following a portal system injection of either Ad/(GIRE)$_3$BP-1 2xfur, or an empty adenoviral vector, animals made diabetic with either low (120 mg/kg), or high (290 mg/kg) dose streptozotocin (STZ) were monitored for changes in body weight, and blood glucose. Without subcutaneous insulin injections, blood glucose values of sham-treated animals (n=8) remained elevated, and animals failed to gain weight (n=4), or died (n=4). In contrast, body weight of Ad/(GIRE)$_3$BP-1 2xfur-treated animals (n=13) increased, and blood glucose remained at near normal levels from one to twelve weeks. Glucose values <50 mg/dl were infrequently observed, and no Ad/(GIRE)$_3$BP-1 2xfur-treated animal succumbed to hypoglycemia. Treatment with the insulin transgene enabled diabetic animals to reduce blood sugars following a glucose load, and to maintain blood sugar levels during a 10-hour fast. Hepatic production of human insulin produced near normal glycemia, and weight gain, without exogenous insulin, and without lethal hypoglycemia.

To verify the efficacy of the promoter of the invention, in a model system more similar to human diabetes mellitus, a virus containing an insulin transgene driven by our promoter was administered to BB Wor rats. Following the onset of autoimmune diabetes mellitus, BB Wor animals treated with exogenous insulin demonstrated wide fluctuations in blood glucose, and sporadic weight gain. Withdrawal of exogenous insulin injections uniformly precipitated the recurrence of ketosis, as indicated by the detection of urine ketones. In contrast, diabetic animals treated by peripheral administration of our virus maintained near normal blood glucose values for more than two months, without exogenous insulin injections. Transgene treated animals were able to tolerate a 24-hour fast without worsening hypoglycemia, and were able to normalize blood sugars following a 2 gm/kg intraperitoneal glucose tolerance test within three hours.

The utility of the promoter of the invention to appropriately regulate the production and secretion of transgenic insulin from hepatocytes both in vitro, and in vivo, was demonstrated by utilizing transcription to control transgene expression. We believe that our novel, chimeric promoter possess the capacity to regulate transgenic production from liver cells in response to metabolic signals of insulin need.

BRIEF DESCRIPTION OF THE DRAWINGS

The above and other objects, novel features and advantages of the present invention will become apparent from the following detailed description of the invention, as illustrated in the drawings, in which:

FIGS. 13A and 13B illustrate the effect of glucose, and its withdrawal, on insulin secretion from stably transfected H4IIE hepatoma cells;

DETAILED DESCRIPTION OF THE INVENTION

We hypothesized that transcriptional regulation of transgenic insulin production would be feasible, but that to be successful, insulin expression should be restricted to a single tissue, must be sufficient to fulfill metabolic requirements, and must be sufficiently regulated to both avoid lethal hypoglycemia, and accommodate glucose loads. To satisfy these requirements, a family of chimeric promoters composed of the Insulin-like Growth Factor Binding Protein-1 (IGFBP-1) basal promoter, and multimers of the glucose response element (GIRE) of the liver-pyruvate kinase (L-PK) promoter, was designed and constructed. IGFBP-1 was chosen for an expression largely restricted to the liver, its robust production, and characteristics of its metabolic regulation (References 19-25).

The liver possesses a prodigious synthetic capacity, is readily accessible as a site for viral gene transfer, and is the first recipient of nutrient blood flow from the intestinal tract. This location provides a theoretical advantage in the early detection of glucose influx into the circulatory system. Moreover, the liver is also the only extra-pancreatic tissue that expresses proteins critical to the metabolic sensory mechanism known to control insulin secretion from β-cells, the GLUT-2 protein, and the high $K_m$ hexokinase, glucokinase (References 26-27). In the liver, the IGFBP-1 promoter mediates a robust production of IGFBP-1. Densitometric scanning of Western ligand blots indicates a stimulated secretion of rIGFBP-1 from cultured hepatocytes of ~120 µg/24 hr/3.6× $10^6$ cells, or $10 \times 10^{-16}$ mol/24 hr/cell (Reference 28). Such calculations suggest that only a small percentage of hepatocytes would be required to produce insulin to provide circulating physiologic levels. Yet the expression of IGFBP-1 is tightly regulated at the level of transcription (Reference 25). Glucocorticoids stimulate IGFBP-1 gene expression, as do stimulators of cAMP production (Reference 23). However, these stimulated activities appear to all be subordinate to the inhibitory effects of insulin (Reference 29). Experiments using hepatocytes in vitro indicate that 90% of IGFBP-1 transcription is inhibited within 15 minutes of exposure to insulin, and that this effect predominates over the stimulation produced by either cAMP, or glucocorticoids (References 30-31).

Figure 1A:
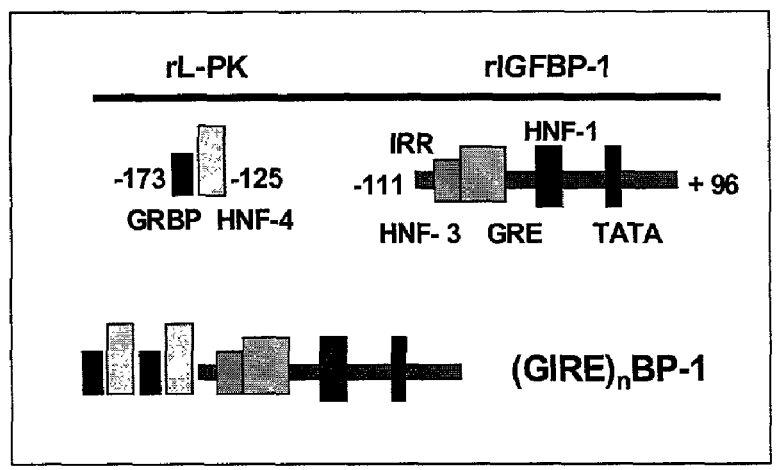
FIGS. 1A and 1B are schematic drawings showing the origin of sequences, and the binding sites for known DNA-binding proteins, comprising the chimeric (GIRE)$_n$BP-1 promoters, and construction of (GIRE)$_n$BP-1 promoter driven luciferase plasmids.
Figure 1B:
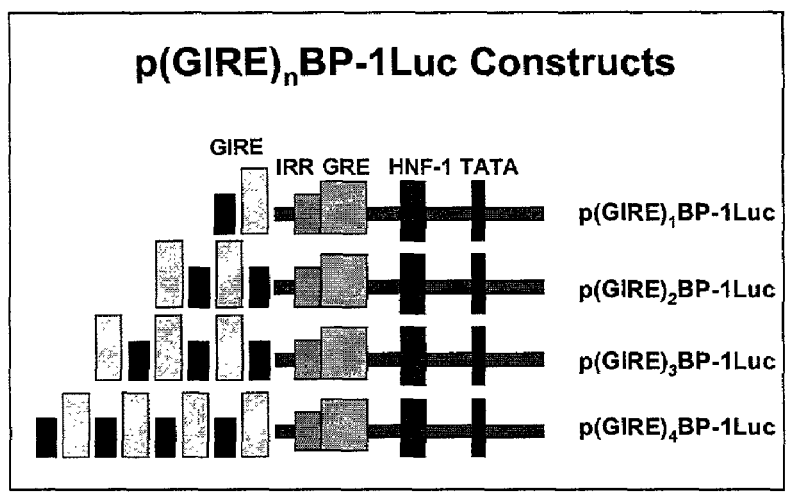

To confer stimulation by glucose to the IGFBP-1 promoter, a characteristic we believed critical to the function of an insulin transgene, a family of promoters was constructed, which are active in hepatocytes, stimulated by glucose, and inhibited by insulin. The glucose response element (GIRE) of the rat L-PK gene was inserted directly upstream of the insulin sensitive element of the rat IGFBP-1 (BP-1) basal promoter. (FIG. 1A). These promoter constructs, inserted into a luciferase expression vector, vary with respect to the number of GIRE sequences present, and their orientation. For example, FIG. 1B illustrates constructs with one to four repeat units of the compound GIRE. In p(GIRE)$_1$BP-1Luc and p(GIRE)$_4$BP-1Luc the L-PK sequences remain in their native orientation, whereas they are reversed in p(GIRE)$_2$BP-1Luc and p(GIRE)$_3$BP-1Luc (FIG. 1B). Within each construct all GIRE sequences, share the same orientation. Like IGFBP-1, L-PK expression is restricted to the liver, and is regulated largely at the level of transcription (Reference 32). In contrast to IGFBP-1, investigators have localized a GIRE within the first 200 base-pairs upstream of the transcription start site (Reference 33). The GIRE is a compound element, comprised of an hepatic nuclear factor-4 (HNF-4) binding site, and an actual GIRE that binds the Glucose Response Element Binding Protein (Reference 34). While active as an isolated element, function of the GIRE is enhanced by juxtaposition to the HNF-4 binding site (Reference 35). Transcriptional activation via the compound GIRE is stimulated by exposure to glucose, but not lactate or fructose, and this stimulation can be inhibited by either co-stimulation of cells with glucagon, or intracellular production of an inhibitory transcription factor, COUP-TF (Reference 35).

To validate the function of the promoters of the invention, their response to various metabolic signals of insulin need was tested. Initial observations and characterization confirming our hypothesis were obtained in vitro utilizing both immortalized cell lines and primary cultured hepatocytes.

Response of p(GIRE)$_n$BP-1Luc Constructs to Glucose and Insulin

Figure 2:
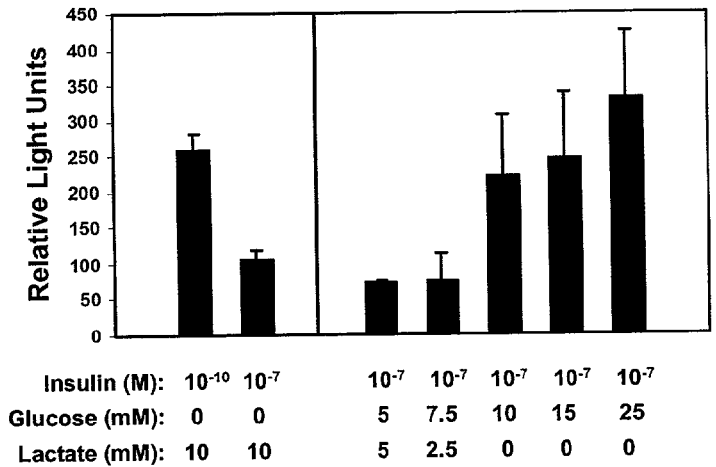
FIG. 2 is a graphical illustration of glucose responsiveness of p(GIRE)$_2$BP-1Luc as determined by transient transfection assay.

As a first evaluation of the transcriptional activity of our constructs, the response of a representative promoter to both insulin and glucose in vitro was tested (FIG. 2). Rat hepatocytes in primary culture transfected with p(GIRE)$_2$BP-1Luc, and pCMVβgal as a control for transfection efficiency, were incubated in either $10^{-10}$M or $10^{-7}$M insulin; concentrations known to span the range of insulin inhibitory effects with respect to the IGFBP-1 promoter in vitro. Reporter activity is reported as a ratio of luciferase to β-galactosidase activity. Results are the means±SEM of three independent experiments, each with triplicate plates. When cells were provided lactate (10 mM), which does not stimulate the GIRE (Reference 35), promoter activity was suppressed approximately 60% in the presence of $10^{-7}$M insulin, indicating function of the insulin response region (IRR) within the IGFBP-1 promoter. Replacing lactate with increasing amounts of glucose resulted in a 3-fold increase in promoter activity, indicating function of the L-PK-derived glucose response elements. Each of the (GIRE)$_n$BP-1Luc constructs was inhibited by insulin, and stimulated by glucose. Glucose concentrations were chosen to span the normal range in both humans (75-140 mg/dl) and rats (110-387 mg/dl). The fact that glucose increased expression in the face of an inhibitory concentration of insulin ($10^{-7}$M) demonstrates that GIRE-mediated stimulation is not subordinate to suppression by insulin.

Figure 3:
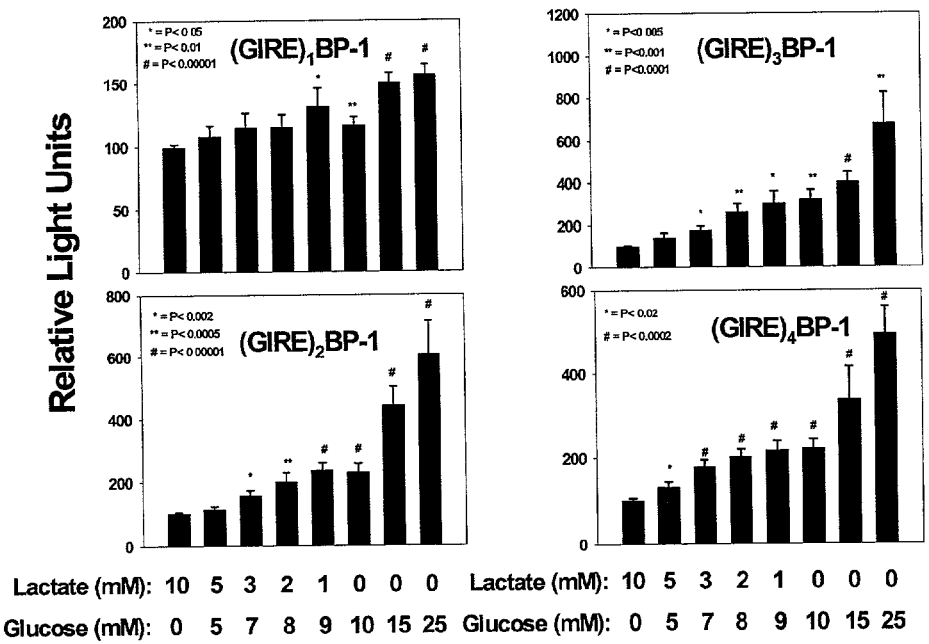
FIG. 3 is a graphical illustration showing comparative response of p(GIRE)$_n$BP-1Luc constructs to stimulation by glucose.

Glucose dose response studies were performed for each of the four promoters to determine if the number of GIRE's present affect the magnitude or kinetics of the response. Primary hepatocytes were co-transfected with the p(GIRE)$_n$BP-1Luc constructs and pCMVβgal, and parallel plates were supplied with either lactate, or increasing concentrations of glucose during an overnight incubation. Promoter response was calculated as a ratio of luciferase to β-galactosidase activity. Results are the means±SEM from a minimum of three independent experiments, each with triplicate plates. Increasing glucose concentrations induced a progressive increase in normalized reporter activity for each of the constructs in the presence of $10^{-7}$M insulin (FIG. 3). While the presence of a single glucose response element was sufficient to induce a statistically significant glucose response, the magnitude of this response increased with the copy number of GIRE's. In this series of experiments, exposing cells to 25 mM glucose stimulated expression to levels ranging from 1.6 fold for p(GIRE)$_1$BP-1Luc, to a maximum of 6.4-fold for p(GIRE)$_3$BP-1Luc, when compared to baseline. In contrast to the variability in maximal stimulation, all constructs appeared to share a similar sensitivity to glucose, and responded across the tested range of 5-25 mM.

Figure 4:
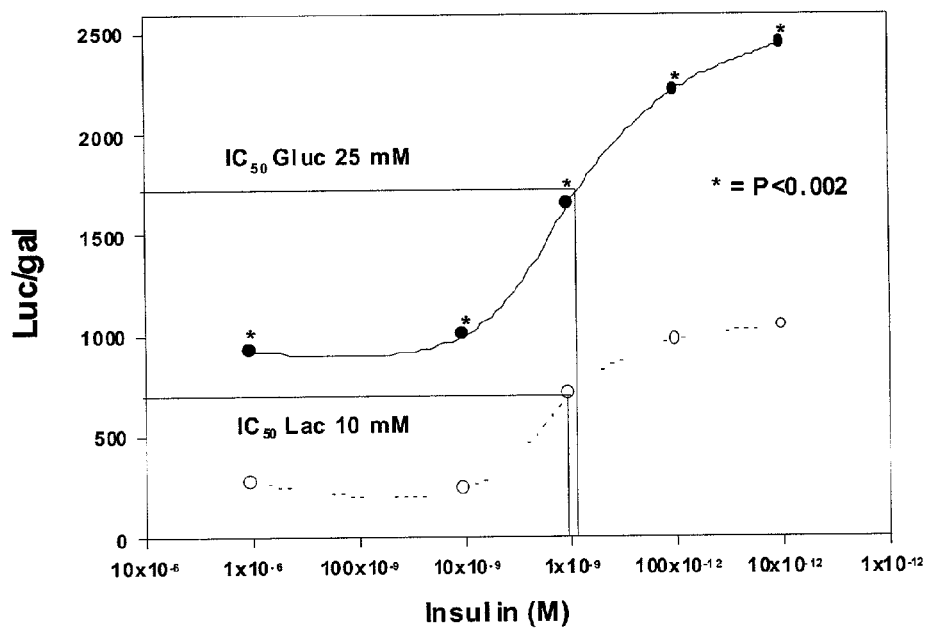
FIG. 4 illustrates comparison of insulin dose response curves for p(GIRE)$_2$BP-1Luc performed with lactate or glucose.

The increased expression observed following exposure to glucose is presumably due to transcriptional stimulation mediated by the GIRE. However, a glucose dependent mechanism that diminishes insulin-mediated inhibition might produce similar results. To distinguish between GIRE mediated stimulation, and inhibition of the insulin response region, hepatocytes transfected with p(GIRE)$_2$BP-1Luc were treated with increasing amounts of insulin ($10^{-11}$ to $10^{-6}$ M), and supplied with either 10 mM lactate (open circles) or 25 mM glucose (closed circles) as a carbohydrate source (FIG. 4). Promoter response was calculated as a ratio of luciferase to β-galactosidase activity. Results are representative of three independent experiments, and show the means of triplicate samples. At all insulin concentrations reporter activity was two-three fold greater in cells exposed to glucose than in cells provided lactate. Moreover, the proportional increase in activity induced by glucose was similar across the entire range of insulin concentrations. As determined from the plotted data, the insulin concentration associated with a 50% inhibition of activity (the IC$_{50}$) was approximately $10^{-9}$M.

Time Course of p(GIRE)$_3$BP-1Luc Response to Glucose

Figure 5:
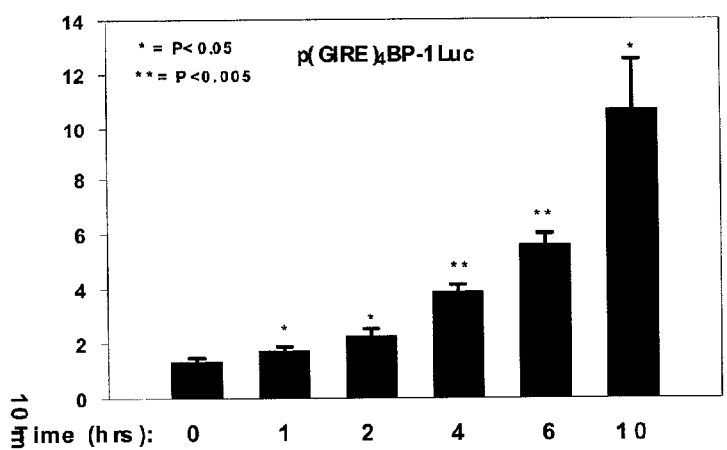
FIG. 5 is a graphical illustration showing time course of (GIRE)$_4$BP-1 promoter driven protein production.

Time course experiments were performed to determine the kinetics of glucose-stimulated expression of a transgene protein. Hepatocytes were transfected with a p(GIRE)$_4$BP-1Luc and cultured in glucose-free medium for 24 hours in the presence of $10^{-7}$M insulin. Medium was replaced with glucose-containing medium (25 mM) at time 0, and cells were harvested at the times indicated. Following exposure to glucose, an increase in the quantity of transgene protein product could be detected in cells transfected with p(GIRE)$_4$BP-1Luc, in as little as one hour, with a progressive increase over the 10 hour period examined (FIG. 5). Hepatocytes were co-transfected with p(GIRE)$_4$BP-1Luc and pCMVβgal. Results are means±SEM for triplicate plates, and are expressed as a ratio of luciferase to βgalactosidase activity.

Stimulation of a p(GIRE)$_n$BP-1Luc Construct by Glucocorticoids

Figure 6:
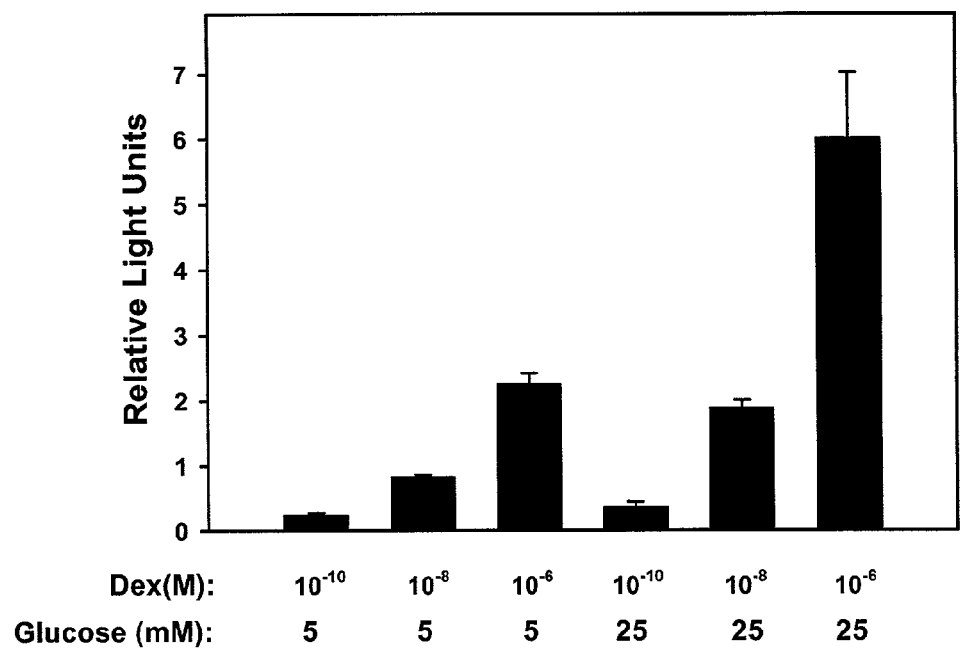
FIG. 6 is a graphical illustration of a glucocorticoid response wherein hepatocytes transfected with p(GIRE)$_2$BP-1Luc were exposed to a serum-free medium containing insulin $10^{-9}$M, with dexamethasone and glucose as indicated.

Since the insulin response region within the IGFBP-1 promoter overlaps with a stimulatory glucocorticoid response element, (Reference 36), we hypothesized that glucocorticoids would also stimulate our chimeric promoter. To test this, hepatocytes in primary culture were transfected with p(GIRE)$_2$BP-1Luc, and exposed to increasing concentrations of the glucocorticoid dexamethasone, while in either low (5 mM) or high (25 mM) glucose medium. Analysis of luciferase reporter gene expression demonstrated that dexamethasone stimulates the (GIRE)$_2$BP-1 promoter in a dose dependent fashion (FIG. 6). Moreover, reporter activity at a given concentration of dexamethasone was greater when cells were exposed to the higher glucose concentration. Thus, glucocorticoid stimulation appears to enhance the stimulation afforded by exposure to glucose.

Glucagon Inhibits Glucose Mediated Stimulation of p(GIRE)$_n$BP-1Luc Constructs

Figure 7:
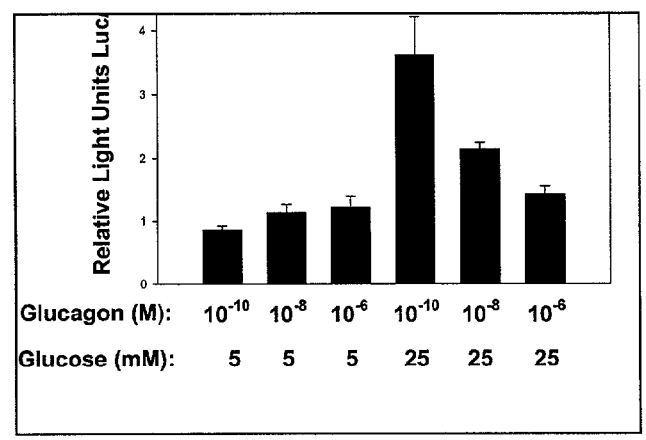
FIG. 7 is a graphical illustration of glucagon effects on (GIRE)$_n$BP-1 promoter/enhancers.

We next evaluated the affect of glucagon on (GIRE)$_n$BP-1 mediated transcription. Glucagon increases cAMP production within hepatocytes, which may stimulate IGFBP-1 transcription via cAMP response element known to be present within its 5-prime promoter (Reference 37). However, cAMP is believed to inhibit the stimulatory affect of glucose on the L-PK promoter (Reference 38). To determine which of these conflicting effects may predominate with our chimeric promoters, hepatocytes were transfected with p(GIRE)$_2$BP-1Luc, provided medium containing either a low (5 mM) or high (25 mM) concentration of glucose and $10^{-9}$M insulin. Parallel plates were then exposed to increasing doses of glucagon, and normalized luciferase activity measured following an overnight incubation. Advancing glucagon concentrations produced minimal increases in luciferase activity under conditions of low glucose. However, glucagon inhibited the stimulation mediated by high glucose to a significant extent, in a dose dependent fashion (FIG. 7).

Figure 8:
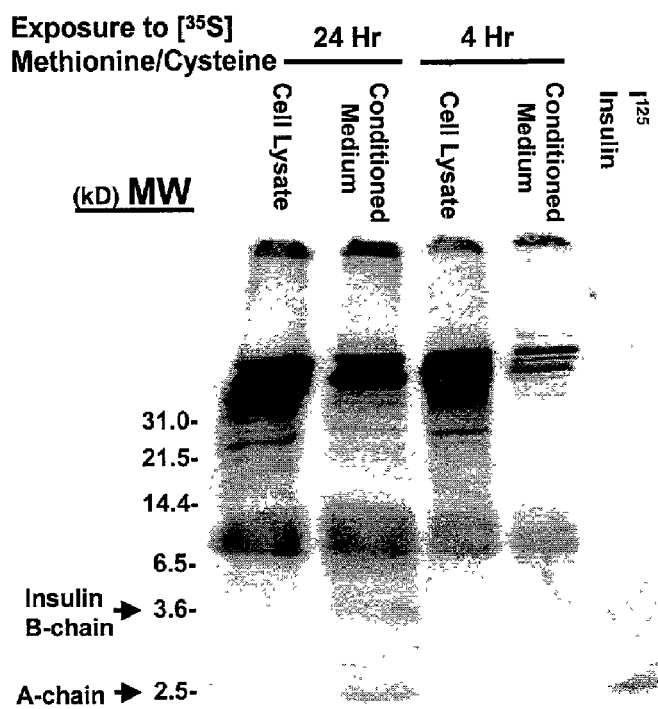
FIG. 8 illustrates post-translational insulin processing in primary cultured hepatocytes.

Hepatocytes Produce Mature Human Insulin Via a Modified Proinsulin Construct Excision of C-peptide from translated proinsulin is a function normally restricted to tissues that express the requisite specific endopeptidases, prohormone convertase-1/3 and prohormone convertase-2 (Reference 39). To enable hepatocytes to process proinsulin to insulin, we obtained a human proinsulin cDNA (2xfur) (Reference 40), modified to allow C-peptide excision by furin, a protease expressed in many tissues including hepatocytes (Reference 41). Following construction of a CMV promoter driven plasmid incorporating the 2xfur sequence (pCMV2xfur), we transfected hepatocytes, and metabolically labeled nascent cellular proteins with [$^{35}$S]-methionine/cysteine. Hepatocytes were labeled for either four, or twenty four hours. Conditioned medium and cell lysates were immunoprecipitated with human insulin specific anti-serum and protein-A-sepharose, then electrophoresed on an 18% sodium-dodecyl-sulfate-polyacrylamide gel, using a 0.4M MESNA loading buffer. Molecular weight markers included the 3.6 kD bovine insulin B-chain, and [$^{125}$I]-mono-iodinated human insulin A-chain. Electrophoresis, under reducing and denaturing conditions, of anti-insulin immunoprecipitates from both cell lysates and conditioned medium revealed a band whose intensity increased between 4 and 24 hours (FIG. 8). With an apparent molecular weight of 9.8 kD the band's extrapolated size is greater than either the insulin A- or B-chain in combination with the C-peptide, but similar to the 9 kD determined for human proinsulin expressed from the same construct in myoblasts (Reference 42). In medium conditioned for 24 hours, immunoprecipitated bands with mobilities identical to the B- and A-chains of insulin are present (FIG. 8); confirming that the insulin transgene product is processed into mature insulin, and that mature insulin is secreted into the culture medium. Independent experiments performed using non-transfected cells failed to reveal the three bands corresponding to insulin products.

Figure 9:
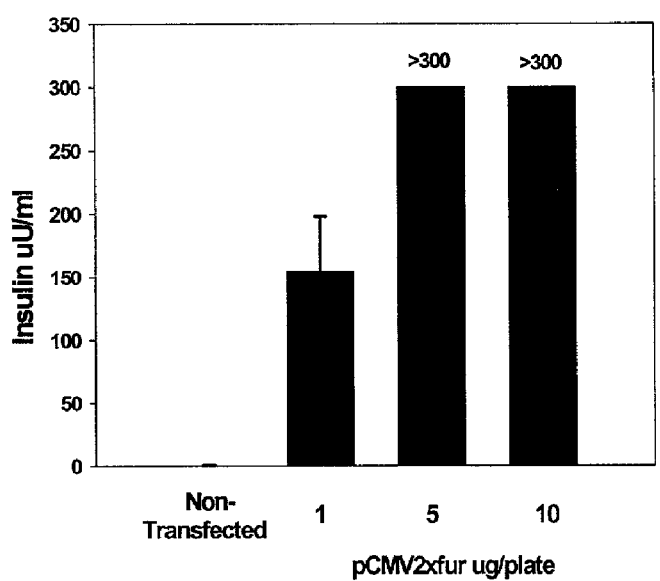
FIG. 9 is a graphical illustration of immunoreactive insulin secretion from hepatocytes.

Medium conditioned by hepatocytes transfected with pCMV2xfur and then assayed for human insulin provides an estimation of the capacity of hepatocytes to produce human insulin. After transfection with 1, 5, or 10 µg pCMV2xfur/60 mm plate, hepatocytes were washed twice in PBS and cultured overnight in serum and insulin free medium. Enzyme-immunoassay performed on an aliquot of the 3 ml of medium per plate conditioned by non-transfected cells demonstrated undetectable levels of immunoactivity. In contrast, 3 ml of medium conditioned by transfected cells produced levels of insulin immunoactivity greater than 10-fold the concentration in fasting human serum (5-20 µU/ml) (Reference 43) (FIG. 9). The immunoassay employed reported an upper limit of detection of 300 µU/ml. The detection of insulin immunoactivity in an assay possessing minimal cross-reactivity with pro-insulin (0.005%, Abbot Diagnostics) provides further evidence of successful proinsulin processing by hepatocytes.

Figure 10:
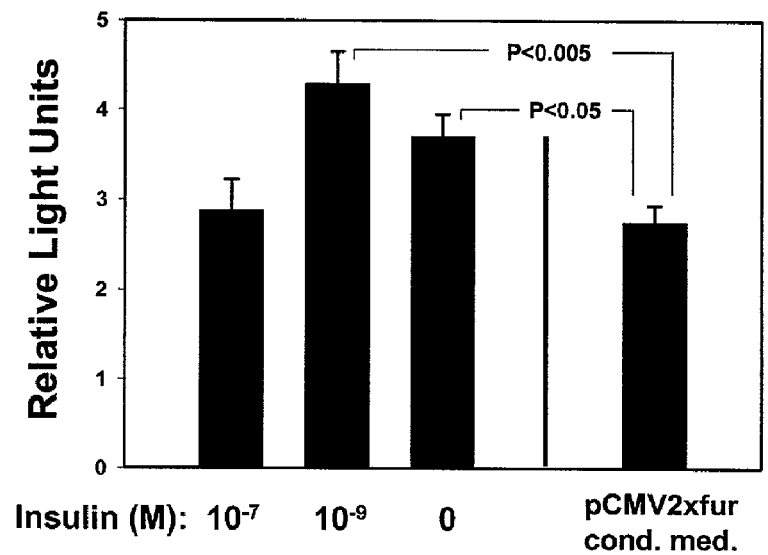
FIG. 10 is a graphical illustration of determination of biological activity for hepatocyte produced insulin.

The biological activity of the transgene of the invention was confirmed by testing the capacity of secreted insulin to inhibit insulin-sensitive reporter gene expression in a transient transfection assay. Primary cultured hepatocytes were co-transfected with pCMVβgal, and p-324-+96BP-1Luc, an insulin suppressible luciferase expression vector driven by the rIGFBP-1 promoter. Cells were cultured overnight in serum free medium containing 10$^{-7}$M insulin. Control cells were provided serum free medium, which had been conditioned overnight by non-transfected hepatocytes, and to which insulin had been added at a concentration of either 0, 10$^{-7}$ or 10$^{-9}$M. Test cells were supplied medium conditioned overnight by hepatocytes transfected with pCMV2xfur (5 µg/60 mm plate), and all cells were harvested for luciferase and β-galactosidase assay following a further overnight incubation. As expected, compared to 10$^{-9}$M insulin, exposure to 10$^{-7}$M insulin inhibits reporter expression driven by the −324-+96BP-1 promoter in control cells (FIG. 10). More significantly, pCMV2xfur conditioned medium also inhibits expression, and the degree of inhibition is consistent with an insulin effect in the conditioned medium on the approximate order of magnitude of 10$^{-7}$M insulin.

Glucose-Stimulated Human Insulin Production in Rat Hepatocytes

Figure 11:
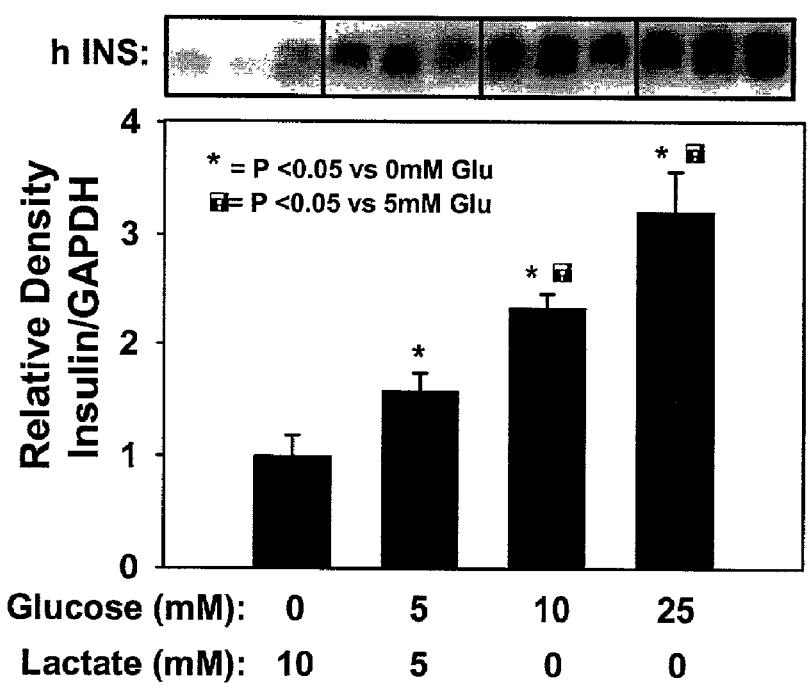
FIG. 11 illustrates glucose stimulation of (GIRE)$_3$BP-1 2xfur mediated human insulin expression in hepatocytes.

We then determined if a glucose and insulin sensitive promoter could mediate glucose responsive insulin production from hepatocytes. We first created a glucose-responsive insulin transgene, (GIRE)$_3$BP-1 2xfur, by replacing the luciferase sequence in p(GIRE)$_3$BP-1Luc with the 2xfur proinsulin sequence. To verify that glucose stimulation occurred at the level of transcription, we performed Northern analysis of primary hepatocytes infected with an adenovirus containing the (GIRE)$_3$BP-1 2xfur sequence. [Ad/(GIRE)$_3$BP-1 2xfur (1–10$^8$ PFU, MOI ~10)]. Total RNA was isolated from transduced cells cultured overnight in serum-, and insulin-free medium containing either lactate (10 mM) or varying concentrations of glucose (5-25 mM). Membranes were sequentially probed for human insulin and rat GAPDH, and the degree of glucose stimulated insulin expression determined by dividing lane specific densitometry measurements for insulin by readings obtained for GAPDH (FIG. 11). Adding glucose to the medium increased insulin expression relative to cells exposed to lactate alone (P<0.05), while increasing glucose from 5 to either 10 or 25 mM stimulated insulin expression still further (P<0.05).

Figure 12:
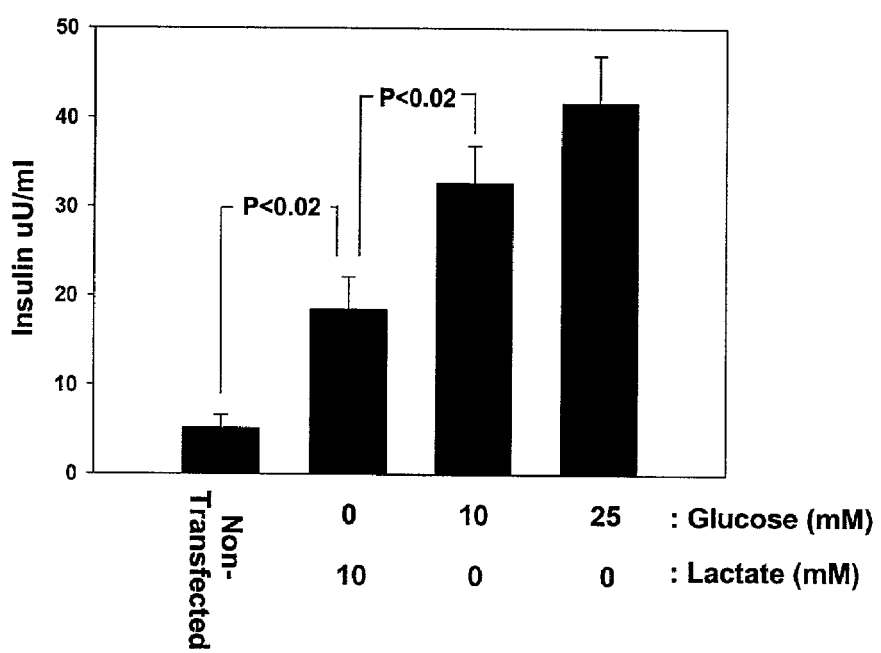
FIG. 12 is a graphical illustration of glucose responsive stimulation of insulin secretion from hepatocytes in primary culture.

Hepatocyte insulin production also increased in response to glucose. Following transient transfection with p(GIRE)$_3$BP-1 2xfur (5 µg/60 mm plate) primary hepatocytes cultured in insulin-free medium were again provided lactate, or varying amounts of glucose (FIG. 12). Insulin immunoactivity was detected in the conditioned medium of non-transfected cells; possibly carried over from incubation with insulin containing medium. Results are the means±SEM combined from three independent experiments. However, medium conditioned by cells transfected with the insulin transgene demonstrated a 4-fold increase in the amount of immunoreactive insulin, even in the absence of glucose. Substituting glucose for lactate in the culture medium stimulated a further dose dependent increase in insulin secretion. The human insulin specific RIA used in these analyses is reported to have minimal cross-reactivity with pro-insulin (<0.2%), supporting the conclusion that p(GIRE)$_3$BP-1 2xfur is able to mediate glucose responsive human insulin secretion from rat hepatocytes in primary culture.

Diminishing transgene expression following transient transfection, and the limited longevity of hepatocytes in primary culture, complicate analysis of extended time-course studies. To overcome these obstacles, and confirm the reversibility of glucose stimulated insulin secretion, we created an insulin secreting hepatoma cell line by stably transfecting H4IIE cells with p(GIRE)$_3$BP-1 2xfur. An insulin-secreting clone, A3, was chosen for further study, and cultured in two groups of triplicate plates in serum- and insulin-free medium. The first group initially received lactate-containing medium, while the second group initially received glucose containing medium. Each group then alternately received two periods of exposure to glucose, and two exposures to lactate. Triplicate wells of A3-cells were provided either 10 mM lactate or 10 mM glucose in an insulin-free medium. Medium was exchanged daily, while the carbohydrate source was altered every two days; cells provided glucose, were changed to lactate, and vice versa. Medium was collected for analysis after two days in each condition, and assayed using a human insulin specific RIA. P<0.02 for (+) Glucose vs. (−) Glucose within each group. Mean±SEM. Assay by human insulin human insulin specific RIA of conditioned medium collected after two days in each culture condition indicated that A3 cells continuously secreted small amounts of insulin under glucose-free conditions (5-10 µU/ml) (FIGS. 13A-B). However, insulin levels in the culture medium were significantly greater during each period of glucose exposure (21-38 µU/ml). Moreover, insulin secretion returned toward baseline upon glucose withdrawal, confirming the reversibility of glucose stimulation in this model. Increased insulin secretion following re-challenge with glucose indicates that reduced insulin secretion following glucose withdrawal was not diminished due to reduced cell viability. The order of exposure is also irrelevant, as insulin secretion increased in response to glucose irrespective of whether cells were exposed first to glucose, or first to lactate.

Summary of In Vitro Experiments

Our results demonstrate that a metabolically sensitive promoter driving expression of a modified proinsulin cDNA can regulate human insulin secretion from hepatocytes in response to glucose exposure. By inserting multimers of the rat L-PK glucose responsive element into the insulin-sensitive IGFBP-1 basal promoter we created a family of promoters whose activity is stimulated by glucose and inhibited by insulin. Because our chimeric promoter/enhancer constructs are novel, we chose to verify the efficacy of individual promoter elements. The results of transient transfection experiments confirm that the GIRE, the IGFBP-1 basal promoter, and its IRR, each remain functional. Exposing transfected cells to glucose produces a dose dependent increase in reporter gene expression at all insulin concentrations (FIGS. 2, 3 and 4). While glucose treatment of hepatocytes could be argued to increase gene expression in a non-specific manner, glucose stimulation of our promoters remains significant when expression is controlled for by co-transfected β-galactosidase activity. With respect to the IRR, insulin inhibits expression of a representative promoter in both the presence and absence of glucose (FIG. 4). These findings appear to exclude the possibility that glucose exposure merely interferes with the suppressive effects of insulin, and are consistent with the fact that such an effect is also not observed with the native IGFBP-1 promoter. Furthermore, a glucose-mediated impairment of insulin inhibition would be expected to produce a shift in insulin sensitivity, and this is not observed. The $IC_{50}$ for insulin suppression is the same in cells exposed to either lactate or glucose, and is similar to that reported for the native rIGFBP-1 promoter (FIG. 4) (Reference 44). Thus, the IRR and the GIRE function independently of one another. The fact that insulin-inhibition in the $(GIRE)_n BP$-1 system does not dominate the stimulatory effects of glucose on transgene expression is noteworthy, since stimulators of the native IGFBP-1 promoter are subordinate to the inhibitory effects of insulin (References 45-46). The concentration of glucose at which stimulation becomes measurable, resides within a range typical of normal rats, from 5 to 9 mM, and appears continuous through values commonly found in rats made diabetic by STZ administration (References 30 and 47). Moreover, stimulation increases continuously throughout the tested range of glucose concentrations (FIG. 3).

Ad/(GIRE)$_3$BP-1 2xfur Transduced Hepatocytes Secrete Human Insulin In Vitro

Figure 14:
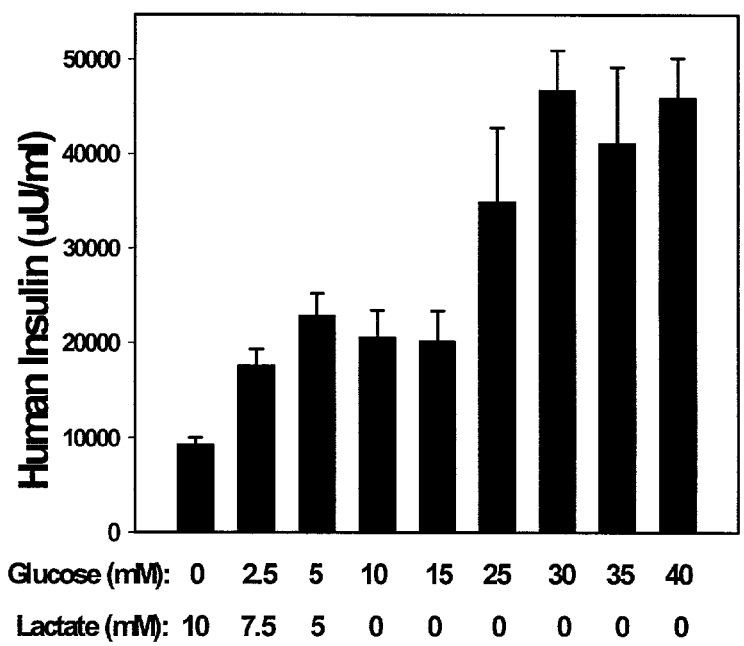
FIG. 14 is a graphical illustration of glucose responsive secretion of human insulin by primary cultured rat hepatocytes.

To confirm the applicability of the data obtained from in vitro experiments in animal models of diabetes mellitus we first developed an adenoviral vector containing an insulin transgene driven by our invention. The capacity of the Ad/(GIRE)$_3$BP-1 2xfur adenoviral vector to confer metabolic responsive insulin production was verified in vitro by infecting rat hepatocytes in primary culture. Following overnight incubation in a glucose-free medium containing lactate (10 mM), hepatocytes transduced with Ad/(GIRE)$_3$BP-1 2xfur (MOI=10) were provided a medium again containing lactate (10 mM), or increasing concentrations of glucose, as shown. Conditioned medium was tested for the presence of human insulin by RIA after an additional overnight incubation. Results are means±SEM of triplicate plates, and are representative of two independent experiments. Insulin in the conditioned medium increased in response to increasing glucose exposure. Confluent hepatocytes in a 60 mm dish provided lactate alone secreted 9.29±0.71 SEM mU/ml immunoreactive insulin. In contrast, cells exposed to 30 mM glucose produced an average of 46.76±4.26 SEM mU/ml insulin during the same overnight incubation (FIG. 14).

The correlation between glucose and insulin secretion was dose dependent, with an $ED_{50}$ of approximately 20 mM glucose, and achieved a maximum between 30 and 40 mM glucose.

Ad/(GIRE)$_3$BP-1 2xfur Administration Produces Glucose Responsive Hepatic Insulin Secretion In Vivo With a functional adenoviral vector in hand, we verified its ability to confer glucose responsive hepatic insulin expression in animals made diabetic with (streptozotocin) STZ, a β-cell toxin. Two to four days following intravenous injection of STZ (120-125 mg/kg) rats received a portal system injection of either Ad/(GIRE)$_3$BP-1 2xfur (2-3.9×10$^9$ PFU), or an equivalent quantity of adenoviral vector without a transgene (Addl312). Exogenous insulin treatment was continued for 2-6 days, and then discontinued. Animals were sacrificed while receiving no exogenous insulin.

Figure 15A:
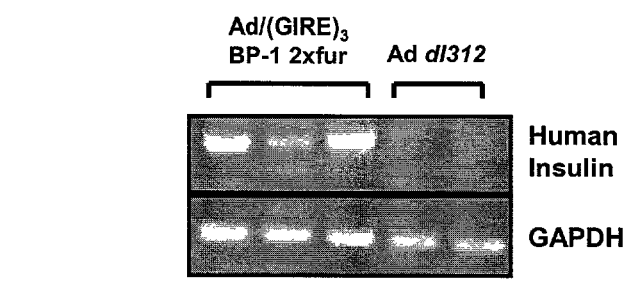
FIGS. 15A and 15B illustrate glucose stimulated human insulin expression following Ad/(GIRE)$_3$BP-1 2xfur administration in vivo.

Following portal system administration of Ad/(GIRE)$_3$BP-1 2xfur to STZ-treated rats, hepatic transgene expression was verified by RT-PCR. In reactions using primers specific for GAPDH, amplification of total liver RNA revealed a 300 bp fragment in three animals treated with Ad/(GIRE)$_3$BP-1 2xfur, and two animals treated with the empty adenoviral vector Ad dl312 (FIG. 15A). However, insulin specific primers produced a 356 bp fragment only in reactions containing RNA from Ad/(GIRE)$_3$BP-1 2xfur-treated livers. Reactions using RNA from Ad dl312 injected livers failed to produce this band.

Figure 15B:
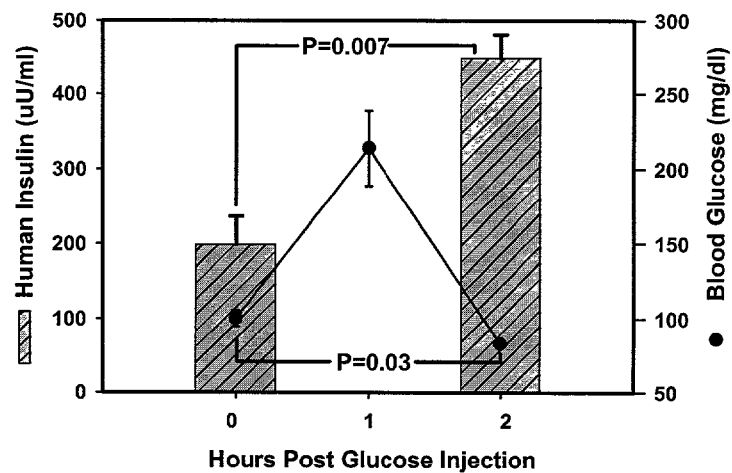

We confirmed transgenic protein production, and glucose responsiveness of the human insulin transgene, by measuring immunoreactive human insulin levels in three Ad/(GIRE)$_3$BP-1 2xfur-treated rats both before, and after glucose administration (FIG. 15B). Following overnight access to food ad libitum, chow was withheld for five hours before animals received intraperitoneal injections of 3 cc 50% glucose. Blood sugar was determined immediately before, and at one and two hours, after glucose administration. Following a five-hour fast the average blood glucose in these diabetic rats was 100 mg/dl. As expected, glucose administration increased serum blood sugar levels, to an average 213 mg/dl at one hour. However, by two hours this value had again fallen to an average of 83 mg/dl. Thus, two hours after an intraperitoneal injection of glucose the average blood sugar was below that produced by a five hour fast (P=0.04). Serum levels of immunoreactive human insulin averaged 199 µU/ml at time 0, and increased in response to glucose stimulation to 449 µU/ml at two hours (P=0.007 compared to pre-glucose). The serum of normal, untreated rats tested with this assay produced readings of 6.13±1.00 µU/ml (n=3, mean±SEM).

Dose Ranging Study for Ad/(GIRE)$_3$BP-1 2xfur Administration

Figure 16A:
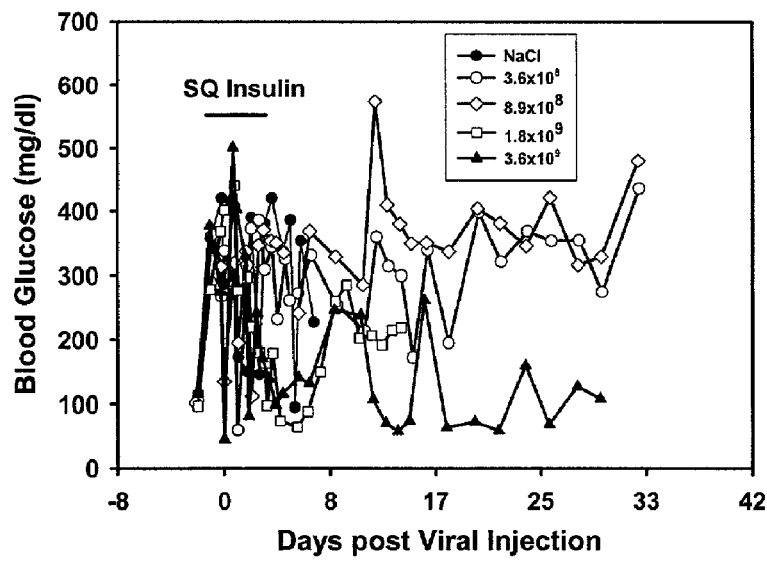
FIGS. 16A and 16B illustrate blood glucose and body weight response to graded dose administration of Ad/(GIRE)$_3$BP-1 2xfur.

To determine which transgene quantities might be effective in controlling glycemia and weight loss due to diabetes, we administered increasing doses of Ad/(GIRE)$_3$BP-1 2xfur to five animals made diabetic with STZ (125 mg/kg). Viral dose ranged from 0 (NaCl 0.9%) to $3.6 \times 10^9$ PFU per animal, and all animals were sustained with exogenous insulin injections for one to six days. Glycemic control in all animals was erratic during the period of exogenous insulin administration. Following discontinuation of injected insulin, random blood sugars tended to vary inversely relative to the administered viral dose. Blood glucose in the control animal increased to >250 mg/dl, and the animal developed ketonuria, weight loss, and died within two days (FIG. 16A). Blood sugars in animals receiving either $3.6 \times 10^8$ or $8.9 \times 10^8$ PFU also remained consistently greater than 250 mg/dl. In contrast, random glucose values in the animal receiving $1.8 \times 10^9$ PFU fell to less than 200 mg/dl for five days following discontinuation of insulin injections, and were less than 200 mg/dl in 25 of 29 (86%) consecutive random measurements in the animal receiving $3.6 \times 10^9$ PFU (FIG. 16A). The animal receiving this highest viral dose, maintained glycemic control for a total of 44 days before developing persistent hyperglycemia.

Figure 16B:
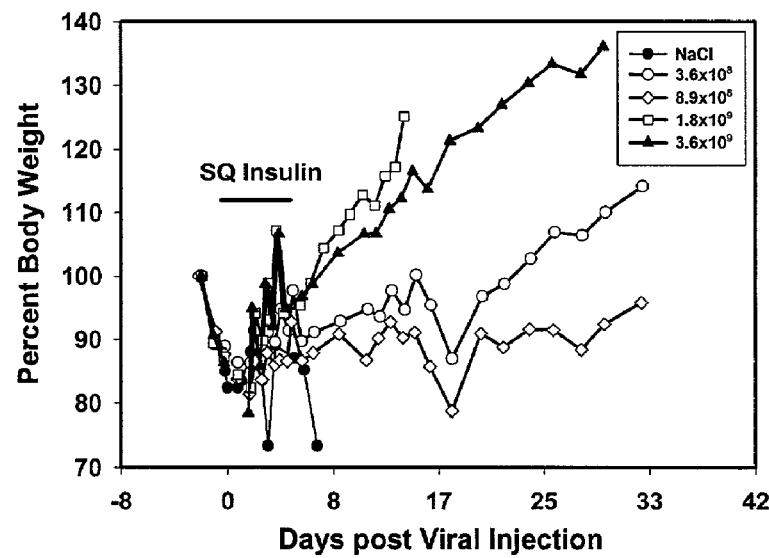

Changes in percent body weight also varied, but in direct relation to viral dose. Animals receiving the two highest viral doses ($1.8 \times 10^9$ and $3.6 \times 10^9$ PFU) steadily gained weight following discontinuation of exogenous insulin. The animal receiving $3.6 \times 10^8$ PFU also gained weight at a diminished rate. The animal receiving $8.9 \times 10^8$ PFU failed to recover weight lost following STZ-injection (FIG. 16B).

Ad/(GIRE)$_3$BP-1 2xfur Treatment Ameliorates Metabolic Abnormalities of STZ-Induced Diabetes Mellitus To determine if transgenic insulin production is sufficient to sustain diabetic animals following withdrawal of exogenous insulin we analyzed data from fourteen animals made diabetic by the injection of 120-125 mg/kg STZ, including the animal receiving $3.9 \times 10^9$ PFU in the dose ranging study. Changes in body weight, and blood glucose of animals treated with Ad/(GIRE)$_3$BP-1 2xfur ($3.4 \times 10^9$-$1.4 \times 10^{10}$ PFU), were compared to animals injected with saline, or the Addl312 vector alone. All animals were supported for two to six days with exogenous insulin injections.

Figure 17A:
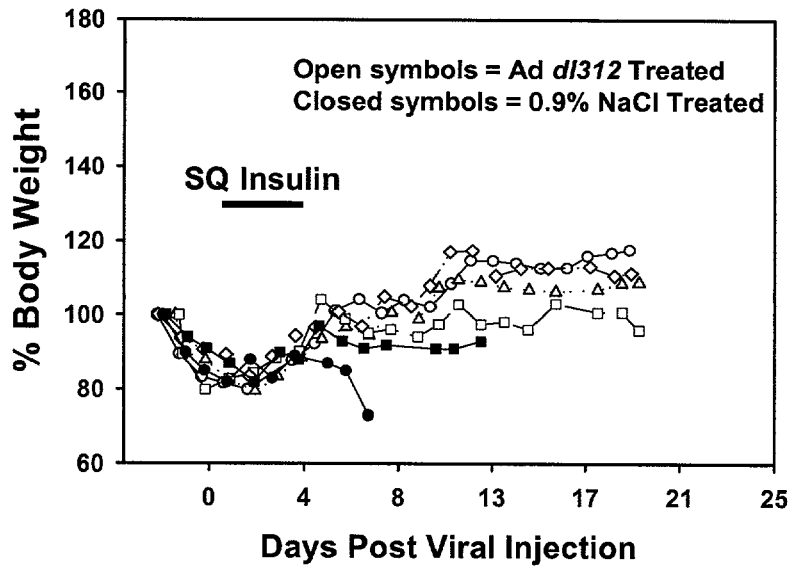
FIGS. 17A and 17B illustrate daily weights of sham treated animals, or diabetic animals treated with Ad/(GIRE)$_3$BP-1 2xfur.
Figure 17B:
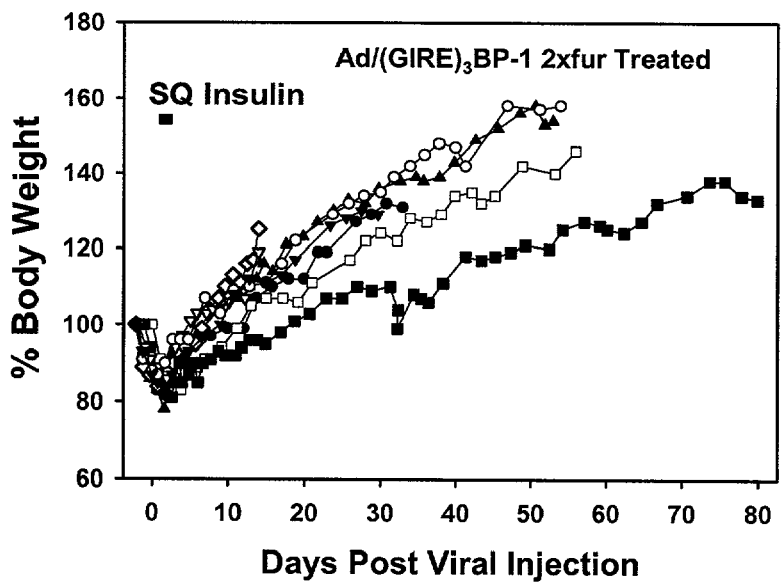

All animals lost weight following STZ injection. Weight loss slowed, or reversed, with the initiation of exogenous insulin injections. Among sham-treated animals weight gain was temporary. Discontinuation of insulin was followed by four days of weight gain, with subsequent stabilization in three Addl312-treated animals (FIG. 17A). A fourth Ad dl312-treated animal, and a NaCl-treated animal failed to gain weight, while the remaining NaCl-treated animal precipitously lost weight (FIG. 17A). Intake and output of the four Ad dl312-treated rats was measured in metabolic cages during six hours of a light period. Average chow consumption was increased 9-fold compared to normal animals. Water intake was 17-fold greater in Ad dl312-treated rats, than in normal animals, while output of stool and urine were increased 2.5 and 9-fold, respectively. In contrast, all Ad/(GIRE)$_3$BP-1 2xfur-treated animals continuously gained weight during a comparable time span, without the plateau observed in sham-treated animals (FIG. 17B). Moreover, weight gain in Ad/(GIRE)$_3$BP-1 2xfur-treated animals continued until sacrifice (14-80 days).

Figure 18:
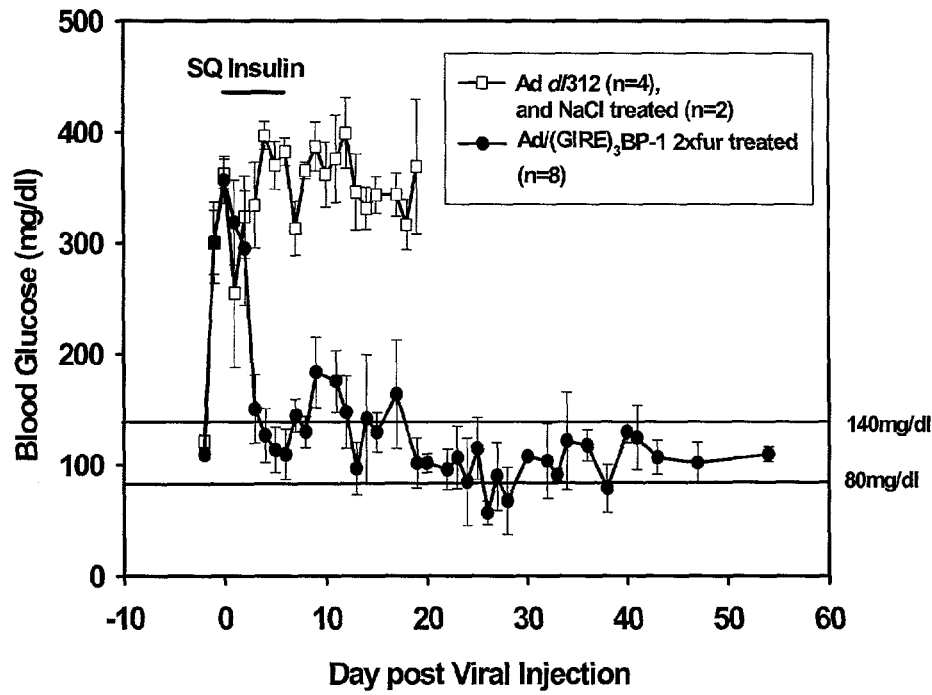
FIG. 18 illustrates mean daily blood glucose values for sham-treated, and Ad/(GIRE)$_3$BP-1 2xfur-treated rats made diabetic with low-dose (120-125 mg/kg) STZ.

In both treatment groups, average daily blood sugars rose sharply following STZ administration, and remained elevated in spite of exogenous insulin administration (FIG. 18). After STZ administration rats received a portal system injection of Ad/(GIRE)$_3$BP-1 2xfur (n=8), Addl312 (n=3), or NaCl 0.9% (n=2). All animals received chow and water ad libitum, and exogenous insulin was administered from 2-6 days. Blood glucose values were averaged across groups. For days in which multiple glucose values were available, the first value of the day was utilized. One control animal died, and three subject animals were sacrificed during the study. Blood sugars obtained after animals again developed hyperglycemia (>250 mg/dl for $\geq$3 consecutive values) were excluded from analysis. Each data point represents the contribution of at least three animals. Results are means±SEM.

Excluding the first 24 hours following discontinuation of exogenous insulin, all blood sugar values of 6 sham-treated animals, except one, were greater than 200 mg/dl. In contrast, levels of blood sugar in Ad/(GIRE)$_3$BP-1 2xfur-treated rats fell within two to four days after viral injection.

The duration of metabolic control produced by treatment with Ad/(GIRE)$_3$BP-1 2xfur was variable, lasting from 7.9 days post-viral injection to 84.9 days post-viral injection. Thereafter, all Ad/(GIRE)$_3$BP-1 2xfur-treated animals redeveloped persistent hyperglycemia (>250 mg/ml for $\geq$3 consecutive measurements). As each animal developed persistent hyperglycemia, the duration of metabolic control was recorded, and elevated blood glucose values were excluded from the calculation of group averages. Sacrifice of three animals during the study reduced the number of animals contributing to daily averages. However, each data point in FIG. 18 utilizes the results of at least three independent animals.

Figure 19:
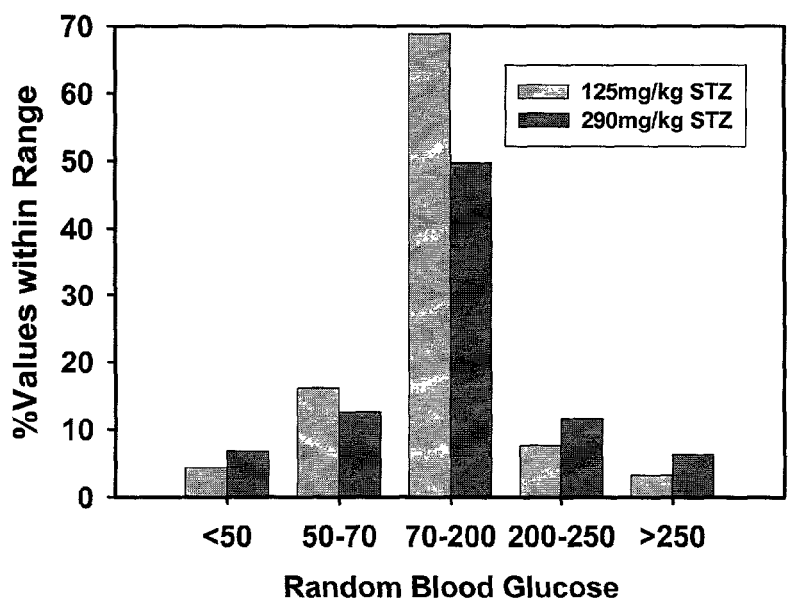
FIG. 19 is a histogram of random blood glucose values for Ad/(GIRE)$_3$BP-1 2xfur-treated rats.
Figures 20A, 20B:
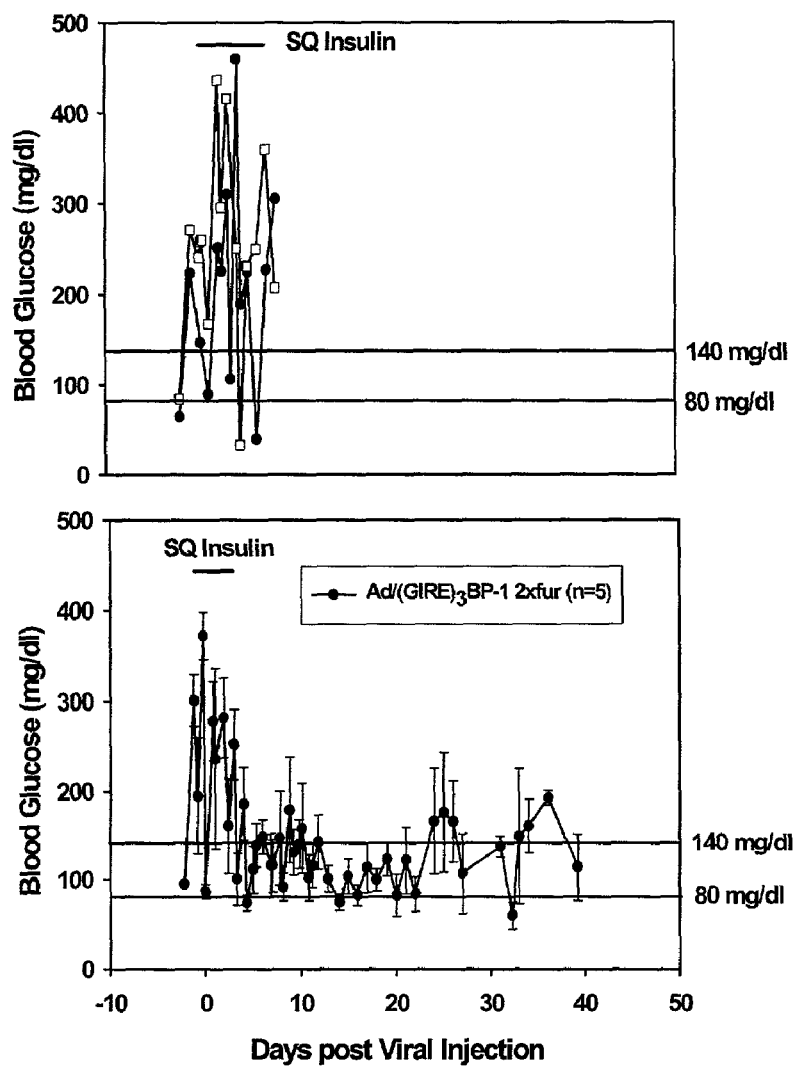
FIGS. 20A and 20B illustrate blood glucose values for sham-treated, and Ad/(GIRE)$_3$BP-1 2xfur-treated rats made diabetic with high-dose (290 mg/kg) STZ.

Mean blood glucose values were significantly lower in Ad/(GIRE)$_3$BP-1 2xfur-treated animals than in sham-treated animals (P<0.05 for 9 of 10 days immediately following discontinuation of exogenous insulin), but fluctuated widely. To obtain a more detailed evaluation of efficacy we examined the frequency distribution of random blood glucose values from Ad/(GIRE)$_3$BP-1 2xfur-treated animals made diabetic with 125 mg/kg STZ. Values obtained within 18 hours of exogenous insulin, or after development of sustained hyperglycemia were excluded (FIG. 19). Random blood glucose values obtained for Ad/(GIRE)$_3$BP-1 2xfur-treated rats were partitioned into five ranges. Of the 186 values available for analysis, 128 (68.81%) fell between 70-200 mg/dl, while 20 values (10.75%) were $\geq$200 mg/dl, and 38 values (20.43%) were $\leq$70 mg/dl. Only 6 values (3.23%) were $\geq$250 mg/dl, and a single value exceeded 300 mg/dl. Severe hypoglycemia,

Ad/(GIRE)₃BP-1 2xfur Treatment Ameliorates Hyperglycemia Induced by High-Dose STZ To reduce the possibility that residual endogenous insulin production had contributed to glycemic control we sought to increase β-cell destruction by increasing the dose of STZ used to induce diabetes from 125 to 290 mg/kg. Seven STZ-treated rats received a portal system injection of Ad/(GIRE)₃BP-1 2xfur (n=5), or Addl312 (n=2). All animals received chow and water ad libitum, and exogenous insulin was administered for two to six days. Blood glucose increased in both animals destined for treatment with Ad/(GIRE)₃BP-1 2xfur, and sham treatment following STZ administration, and fluctuated widely during treatment with subcutaneous insulin. Individual blood glucose values are depicted for sham-treated rats. Upon discontinuation of exogenous insulin, these two animals developed ketonuria, precipitously lost weight, and were euthanized (FIG. 20A). In contrast, the blood sugars in each of the five Ad/(GIRE)₃BP-1 2xfur-treated animals stabilized at levels generally less than 200 mg/dl (FIG. 20B). Blood glucose values for Ad/(GIRE)₃BP-1 2xfur-treated animals are shown as a daily average. For days in which multiple glucose values were available, the first value of the day was utilized. Blood sugars of animals that again developed hyperglycemia (>250 mg/dl for ≧3 consecutive values) were excluded from analysis. Each data point represents the contribution of at least three animals. Results are means±SEM.

We obtained 207 random glucose values later than 18 hours after the last subcutaneous insulin injection, but before the redevelopment of sustained hyperglycemia. (FIG. 19) Of these, 103 values (49.76%) fell within the 70-200 mg/dl range, 40 (19.32%) were ≧70 mg/dl, and 14 (6.76%) were ≧50 mg/dl. An additional 37 values (17.87%) were ≧200 mg/dl, with 13 (6.28%) ≧250 mg/dl. As in the previous group, no animal died of hypoglycemia.

Figure 21A:
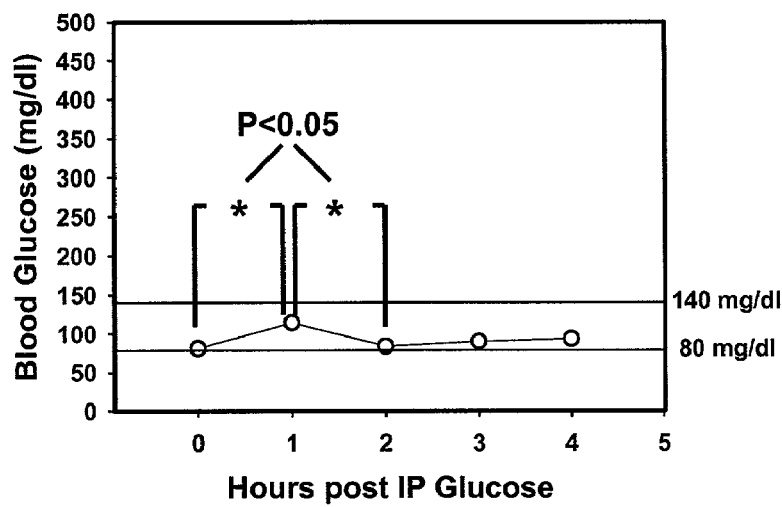
FIGS. 21A and 21B illustrate the effect of IPGTT on blood glucose in normal and diabetic rats treated with Ad/(GIRE)$_3$BP-1 2xfur.
Figure 21B:
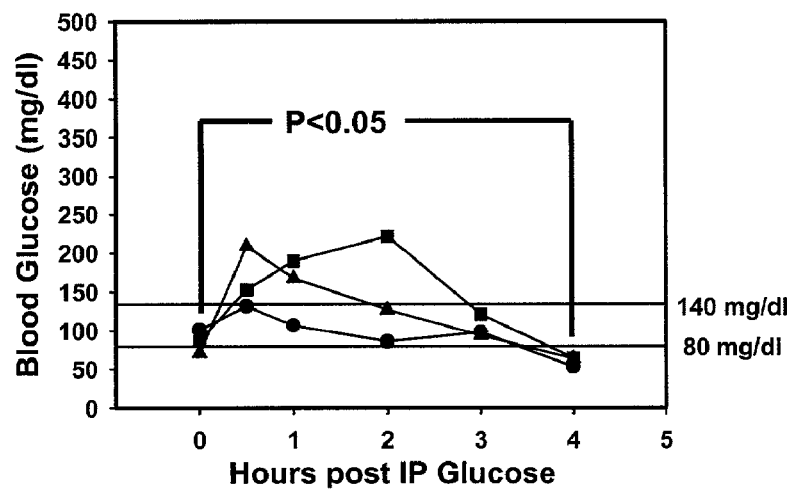

Intraperitoneal glucose-tolerance tests, and ten-hour fasts were used to determine the response of the insulin transgene to environmental variables. After overnight feeding ad libitum chow was withheld for 4.5 hours from each of three rats first made diabetic by high dose (290 mg/kg) STZ, and then treated with Ad/(GIRE)₃BP-1 2xfur. Three normal animals were used as controls. An intraperitoneal glucose tolerance test (IPGTT) was performed by administering 1.35 gm/kg glucose. Prior to injection blood glucose values in normal animals ranged from 71-94 mg/dl (FIG. 21A). They increased significantly by one hour ($P<0.05$, for averages), and returned to baseline by two hours. Baseline blood glucose values in the STZ-treated animals ranged from 71-101 mg/dl (FIG. 21B). Thirty-minute blood glucose values were uniformly elevated, and achieved a maximum in two animals. In these two animals one-hour values had declined, and were less than 140 mg/dl by two hours. All values were between 80-140 mg/dl by three hours, and continued to decline by hour-4.

Figure 22:
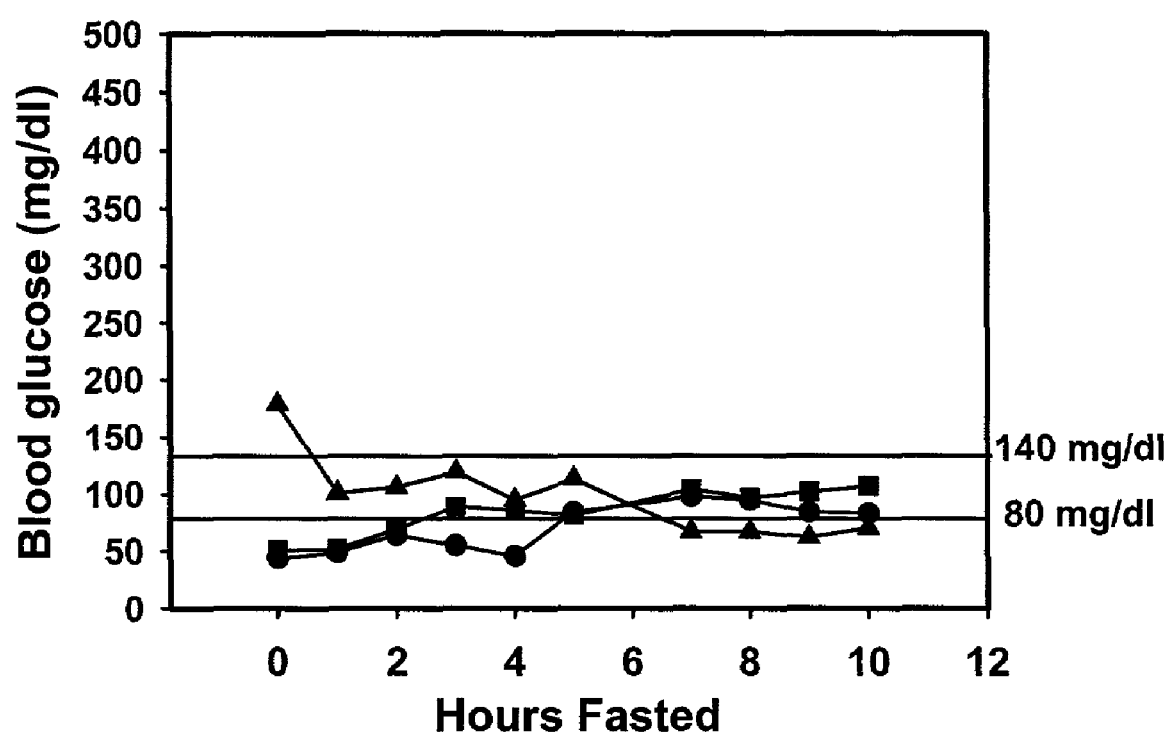
FIG. 22 illustrates fasting tolerance of Ad/(GIRE)$_3$BP-1 2xfur-treated STZ-diabetic rats.

While no transgene-treated animal succumbed to hypoglycemia, sporadic low blood glucose values suggested the potential for over-production of transgenic insulin. To test the ability of treated animals to withstand food deprivation, the three treated animals used in the IPGTT study, were subjected to a more prolonged period of food deprivation. Following overnight access to chow ad libitum, serial blood glucose measurements were obtained while animals were subjected to a ten-hour fast (FIG. 22). Blood glucose values at the beginning of the fast averaged 91.3 mg/dl. Two of the a.m. glucose values were below normal for fed rats (44 and 51 mg/dl) (Reference 48). However, upon withdrawal of chow, blood glucose for these two animals increased over the next five hours, and stabilized within a normal range. The highest blood glucose fell sharply within the first 30 minutes, and subsequently stabilized at approximately 70 mg/dl for the last three hours of the fast.

We first verified that Ad/(GIRE)₃BP-1 2xfur treatment produces a significant, sustained improvement in blood sugars in rats made diabetic with streptozotocin (STZ), a β-cell specific toxin. Following induction of diabetes by administration of 125 mg/kg STZ, diabetic animals were dosed with an empty adenoviral vector, or Ad/(GIRE)₃BP-1 2xfur, an adenovirus containing an insulin transgene driven by our invention. 69% of all random blood glucose measurements obtained before the recurrence of sustained hyperglycemia were between 70-200 mg/dl. Moreover, rates of hypoglycemia were less than observed in two published models of aggressive treatment with exogenous insulin. In a study comparing subcutaneous insulin algorithms for the treatment of STZ-diabetic rats the lowest reported incidence of hypoglycemia was 31%≦70 mg/dl, and 16%≦50 mg/dl, but was attained only with twice daily insulin administration (Reference 49). To achieve normal 24-hour serum insulin profiles in diabetic Wistar rats, Koopmans, et al used continuous intravenous infusion and programmed meals (Reference 50). However, even with this elaborate design, they observed severe hypoglycemia (≦58/mg/dl) in 40% of fasting blood glucose values (Reference 50). By contrast, we observed hypoglycemia of ≦70 mg/dl, or ≦50 mg/dl, in 20% and 4% of all random blood sugars, respectively, without exogenous insulin administration. The degree of metabolic stability produced by our system of regulated transgenic insulin production is further underscored by the capacity of treated animals to tolerate the divergent stresses of glucose loading, and fasting. Following an intraperitoneal glucose load, blood sugars of treated-diabetic rats had fallen to baseline within 3-4 hours, and serum glucose remained stable during a 10 hour period of fasting.

Pancreatic β-cells are known to under go limited regeneration following STZ treatment (Reference 51). However, measured immunoreactive rat C-peptide in serum of STZ-treated rats (125 mg/kg) was in the range for normal fasting animals, i.e. was inappropriately low for hyperglycemic animals. Reducing the contribution of endogenous insulin production by increasing the dose of STZ from 125 to 290 mg/kg produced minimal changes in glycemic control, and even with this higher STZ dose 49.76% of random glucose values were between 70-200 mg/dl. The percentage of random blood glucose values ≦50 mg/dl increased from 4% in the 125 mg/kg STZ group to 7% suggesting a diminished effect of endogenous insulin, but remained less than some aggressive exogenous insulin regimens (References 49-50).

Figure 23:
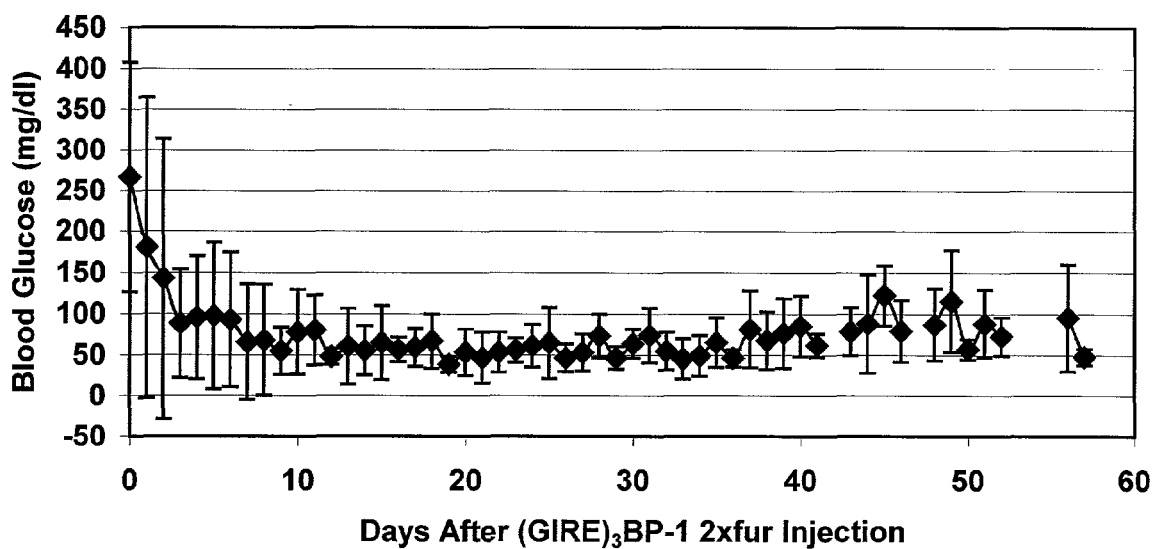
FIG. 23 illustrates that Ad/(GIRE)$_3$BP-1 2xfur treatment ameliorates hyperglycemia in spontaneously diabetic BB Wor rats.
Figure 24:
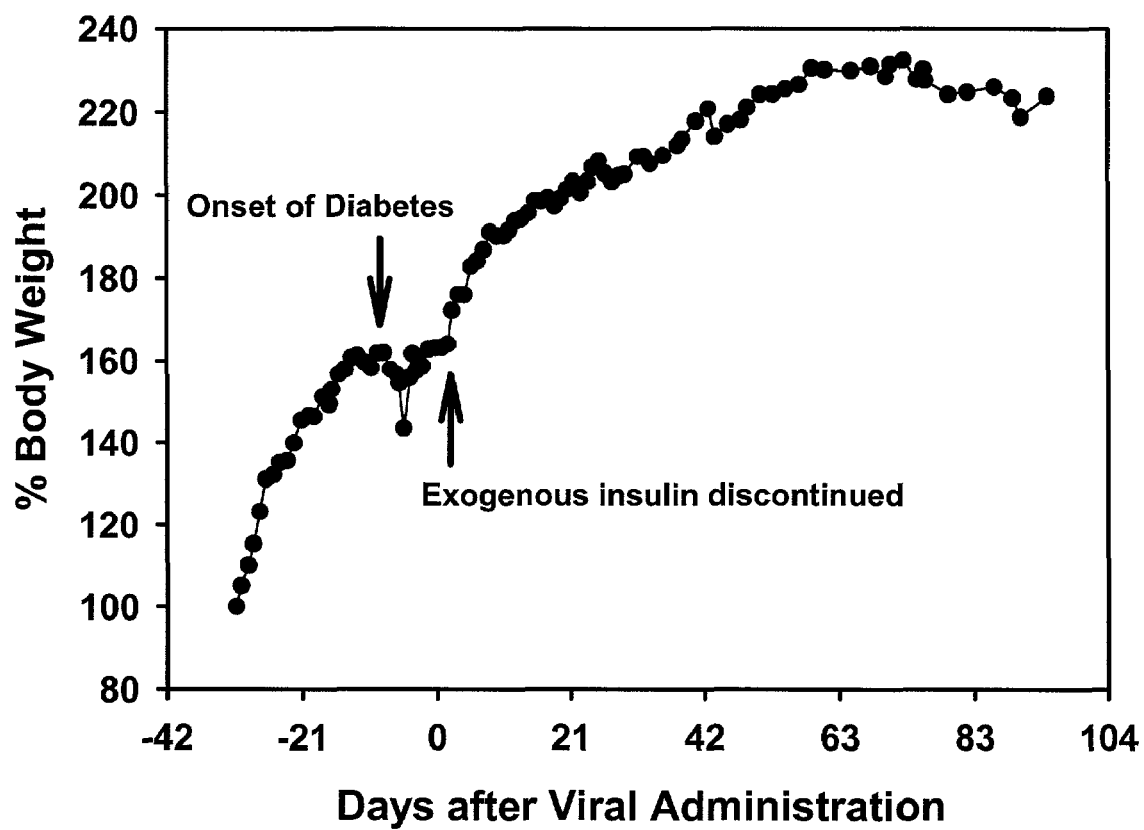
FIG. 24 illustrates that Ad/(GIRE)$_3$BP-1 2xfur treatment induces weight gain in a spontaneously diabetic BB Wor rat.
Figure 25:
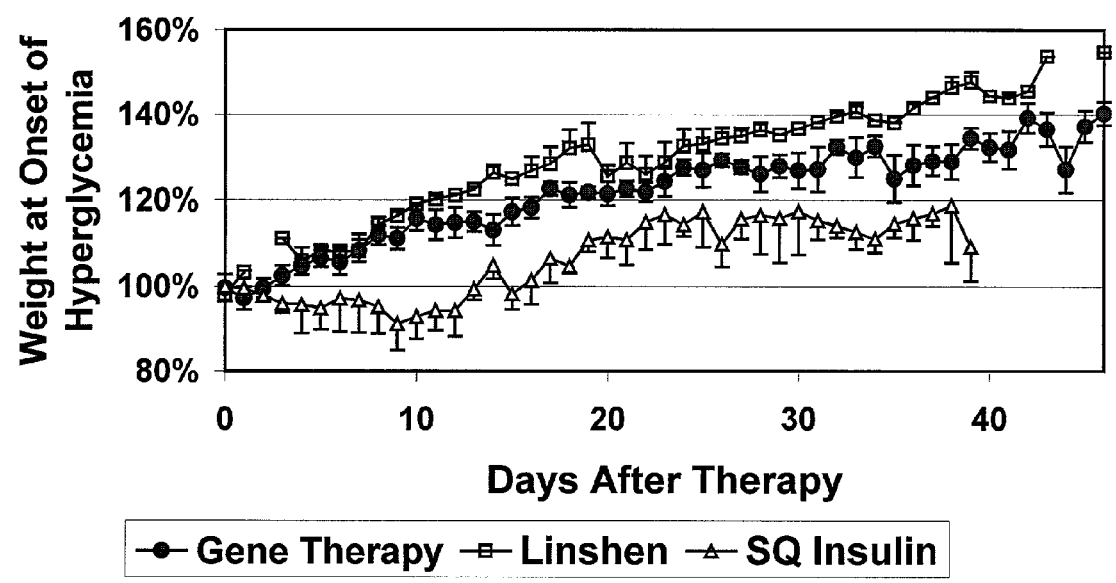
FIG. 25 illustrates that weight gain in Ad/(GIRE)$_3$BP-1 2xfur treated diabetic BB Wor rats is intermediate between the abnormally low weight gain of SQ Insulin treated rats, and the excessive weight gain of diabetic rats treated with continuous release Linshin insulin pellets.

Treatment with Ad/(GIRE)₃BP-1 2xfur Ameliorates Hyperglycemia in Diabetic BB Wor Rats To verify the efficacy of our transgene in a model more representative of human disease, we administered the same adenoviral constructs utilized in the STZ-rat model to BB Wor rats. Diabetes prone (DP) BB Wor rats develop an autoimmune insulitis similar to that seen in human type 1 diabetes mellitus (Reference 52). Between 60 to 80 days of age animals spontaneously become hyperglycemic, fail to gain weight, and left untreated, develop lethal ketoacidosis. Each of twelve DPBB Wor animals were allowed to become diabetic (indicated by whole blood glucose measurements of ≧250 mg/dl on two consecutive days). Following a variable period of treatment with subcutaneous insulin injections ranging from 6 to 29 days, each rat received a jugular venous injection of Ad/(GIRE)$_3$BP-1 2xfur. Viral doses ranged from 1.3 to 4×10$^{10}$ PFU/kg. Within 48 to 60 hours of viral administration exogenous insulin administration was discontinued, and blood glucose levels fell below levels typically sustainable using subcutaneous insulin (FIG. 23). Random blood glucose values were obtained from tail blood using a standard home blood glucose monitor. Results are means±SD for the first daily value. Values from at least three animals contribute to each data point. Blood glucose levels remained depressed despite the cessation of exogenous insulin injections. Moreover, weight gain, which had initially stalled with the onset of hyperglycemia resumed its normal increase following viral administration (FIG. 24). While random blood glucose values were often below normal, no animal succumbed to hypoglycemia. As typified by the a representative animal weight gain plateaus, then reverses, as the animal becomes diabetic during the 8 days prior to administration of Ad/(GIRE)$_3$BP-1 2xfur. Following adenoviral administration, weight gain resumes, despite the fact that exogenous insulin administration has been stopped. In experimental groups twice daily administration of injected insulin (SQ) induced sub-normal weight gain (n=4), while treatment with sustained-release subcutaneous insulin (Linshin) pellets induced mildly excessive weight gain (n=3). (FIG. 25) Weight gain in diabetic, Ad/(GIRE)$_3$BP-1 2xfur treated DPBB Wor rats (n=12) was essentially normal, and intermediate to SQ and Linshin treated animals.

Figure 26A:
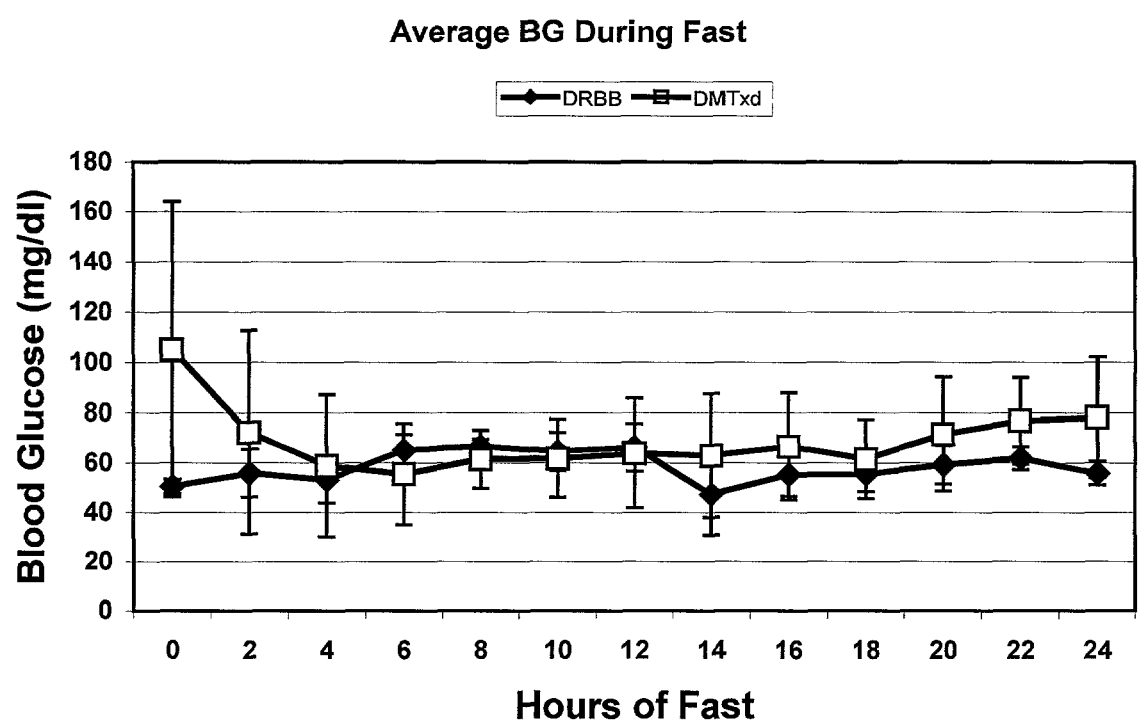
FIGS. 26A and 26B illustrate that Ad/(GIRE)$_3$BP-1 2xfur treated diabetic BB Wor rats withstand prolonged chow deprivation without progressive hypoglycemia, and lose less weight than normal, non-diabetic animals.
Figure 26B:
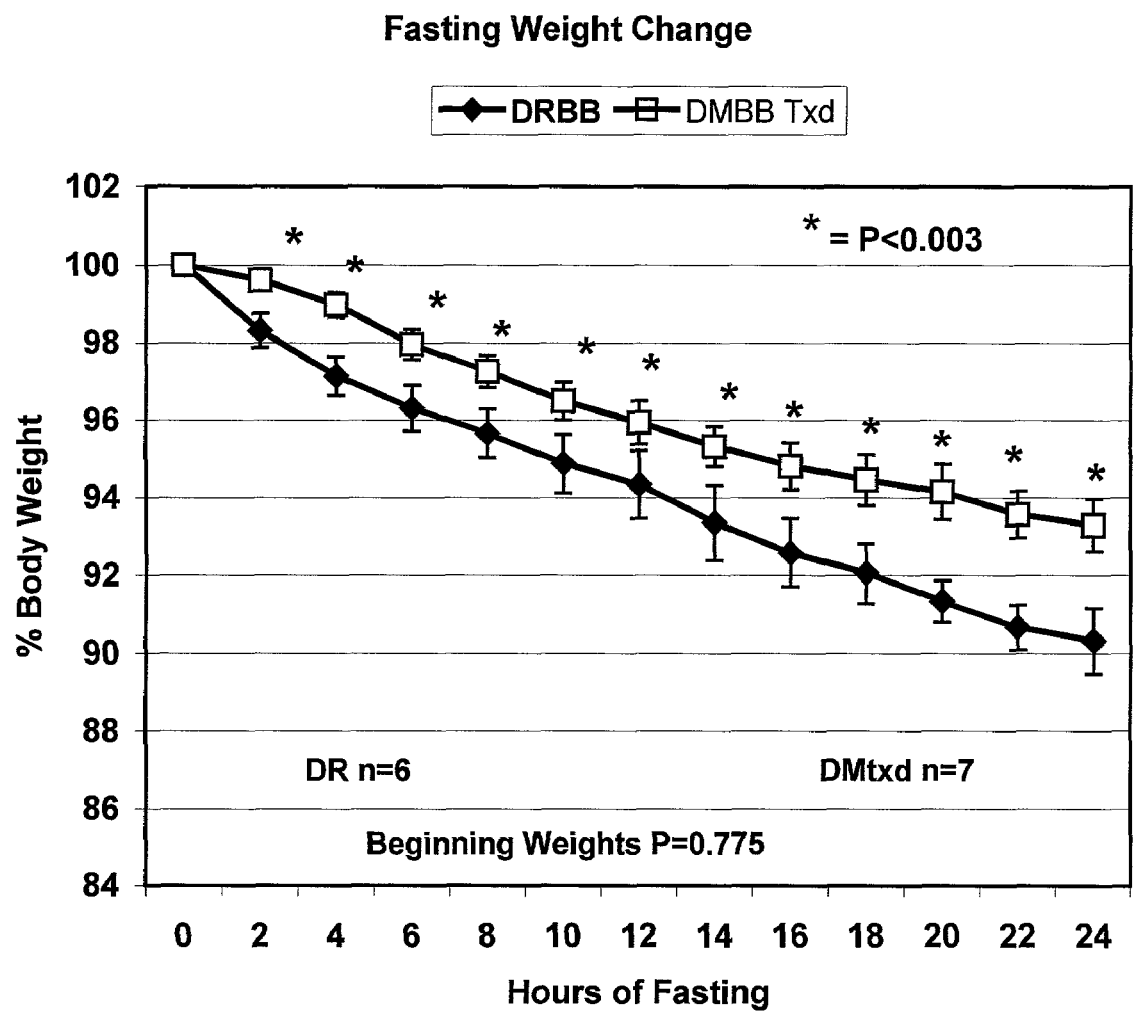

The ability of treated animals to tolerate the metabolic demands of food deprivation, and overfeeding were tested by subjecting them to both a prolonged (24-hour) fast, and an intraperitoneal (IP) glucose tolerance test. All twelve treated diabetes prone (DP)BB Wor rats, and six diabetes resistant (DR)BB Wor rats were deprived of access to food and feces at the beginning of the dark cycle. Weight and blood glucose measurements were then obtained every two, for the following 24 hours. Average blood glucose values of all twelve treated animals tended to decline during the first four hours of the fast, and then stabilized. (FIG. 26A). Results are means±SD for twelve treated DPBB Wor and six non-diabetic DRBB Wor rats. Differences in means failed to reach statistical significance at all but a single time point. Continuously declining body weights measured during the fast confirmed that animals were calorie deprived (FIG. 26B). Despite equivalent average body weight at onset of fasting (P=0.775) non-diabetic DRBB Wor rats progressively lost a greater percentage of body weight than Ad/(GIRE)$_3$BP-1 2xfur treated, diabetic DPBB Wor rats. This difference was significant at all time points, and persisted throughout the observation period. Water intake, and urine output was not different between groups during the same period.

Figure 27:
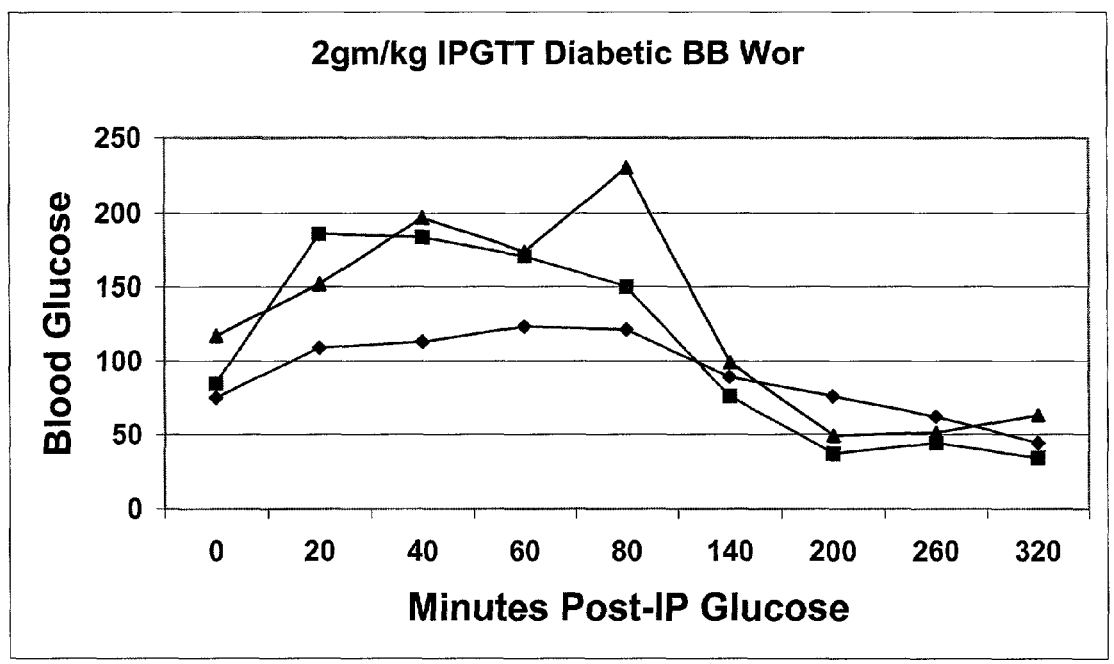
FIG. 27 illustrates that blood sugar of Ad/(GIRE)$_3$BP-1 2xfur treated diabetic BB Wor rats returns to baseline within 140 minutes following an intraperitoneal glucose challenge (2 gm/kg).

Three diabetic animals treated with the insulin transgene were also subjected to an IP glucose tolerance test. Following the administration of glucose (2 gm/kg) the blood sugar of each animal increased. (FIG. 27) However, similar to observations in STZ-treated rats, blood glucose values had returned to baseline levels within 140 minutes. Thereafter, they either continued to decline (one animal) or stabilized (two animals).

In summary, these data confirm, and extend the findings obtained in STZ-treated rats. The spontaneous diabetes mellitus that occurs in DP BB Wor rats is ameliorated following treatment with an insulin transgene driven by our glucose and insulin responsive promoter. Following treatment with the transgene diabetic animals maintain near normal blood sugars, gain weight, and avoid ketoacidosis, all without exogenous insulin. Weight gain in transgene treated animals is less than in animals treated with Linshin continuous-release pellets. Moreover, treated animals are able to tolerate extremes of metabolic demands without adverse events. They were able to sustain acceptable blood glucose levels throughout a prolonged fast, and lost less weight during a fast than non-diabetic animals. They were also able to return blood glucose levels to baseline values within 140 minutes following a large glucose load.

The following materials and techniques were used in the present invention.

Promoter and Viral Constructs

Base pairs −324-+96 of the rat IGFBP-1 promoter were PCR amplified from p-930bpcat (Reference 44), and the product ligated into a TA-cloning vector, pCRII™ (Invitrogen, Carlsbad, Calif.). The primers were as follows, novel restriction sites (Mlu-I in the forward primer, and Nhe-I in the backward primer) are underlined: forward; 5'-GCG ACGCGTTCCCTTAGGTATTCCTTGAGT-TCGG-3' (SEQ ID No.: 7), backward; 5'-GCG GCTAGCTAGTAGCGGAAGTGGTGGTTCACAG-3' (SEQ ID No.: 8). A 526 bp Kpn-I/Xho-I restriction fragment was then directionally inserted into the luciferase expression vector, pGL2Basic (Promega, Madison, Wis.), to create p-324-+96BP-1 Luc. The p(GIRE)$_n$BP-1 Luc plasmids were constructed by inserting copies of the glucose responsive element from the rat L-PK gene into the IGFBP-1 promoter. Oligonucleotides corresponding to 50 bp of the positive (5'-GGGCGCACGGGGCACTCCCGTGGTTC-CTGGACTCTGGCCCCCAGTGT-A-3'-SEQ ID No.: 9) and negative (5'-ATGTACACTGGGGGCCAGAGTCCAG-GAACCACGG-GAG-TGCCCCGTGCGCCC-3'-SEQ ID No.: 10) strands of the rat L-PK GIRE sequence were annealed, multimerized, and size fractionated by polyacrylamide electrophoresis. DNA representing a sequence of GIRE multimers, from one to four, was isolated from excised bands, and blunt-ended by treatment with Klenow. Insertion of GIRE multimers into EcoICR-I restricted p-324-+96BP-1 Luc removed all IGFBP-1 sequences 5, to bp −114, and resulted in placement of GIRE sequences immediately 5' to the IGFBP-1 insulin responsive region. Sequencing of resultant plasmid constructs unexpectedly revealed uniform multimerization of all GIRE elements in a head-to-tail orientation. Blunt-end ligation with p-324-+96BP-1 Luc consequently produced constructs in which all GIRE's were either in the native, or reverse orientation.

An adenoviral vector expressing human insulin, Ad/(GIRE)$_3$BP-1 2xfur, was constructed using the Adeno-Quest kit per manufacturer's instructions (Quantum Biotechnologies, Inc., Montreal, Canada). A Sal-I/Hinc-II fragment of p(GIRE)$_3$BP-1 2xfur containing the glucose and insulin sensitive promoter coupled to the 2xfur sequence was inserted into the transfer vector pQBI-AdBN. Homologous recombination following co-transfection of pAdBN- (GIRE)$_3$BP-1 2xfur and manufacturer-supplied viral DNA into HEK-293 cells permitted isolation of E1a/E1b/E3 deleted adenovirus containing the insulin transgene. We verified the capacity to induce insulin production by screening medium conditioned by primary cultured hepatocytes infected with crude lysates of expanded viral plaques using a human-insulin specific RIA (Linco Research, St. Charles, Mo.). Following three-fold plaque purification, viral preparations were purified by double CsCl density-gradient centrifugation, dialyzed against 10% glycerol/HBS pH 7.4, aliquoted, and stored in this same buffer at −70° C. Viral concentration was determined by the tissue-culture infectious dose method ($TICD_{50}$).

Sequencing

Sequencing of chimeric promoters was performed in the DNA Core Facility of Atlanta VA Medical Center/Emory University, using an Applied Biosystems Model 377 automated sequencer (Perkin Elmer, Foster City, Calif.).

Cell Culture and Transfection

Hepatocytes were isolated from male Sprague-Dawley rats (150 to 200 g, Charles Rivers Laboratories, Wilmington, Mass.) by a modification of the collagenase (Worthington, Freehold, N.J.) perfusion method of Seglen (Reference 53). Briefly, following anesthesia by intra-peritoneal injection of a ketamine/xylazine mixture, the portal vein was canulated with a 20 gauge venous catheter, and the liver perfused with collagenase-buffer for six minutes. Livers were removed en mass, and the cells gently shaken from the perforated hepatic capsule in DMEM/F12 (Mediatech Cellgro, Herndon, Va.) supplemented with 10% fetal calf serum (FCS) (Atlanta Biological, Marietta, Ga.). Hepatocytes ($3.5-5 \times 10^6$ cells) were added to 60 mm plates (Falcon/Becton Dickinson Labware, Lincoln Park, N.J.) coated with rat tail collagen (Sigma, St. Louis, Mo.), and non-adherent cells removed twenty minutes later. Incubations were performed in an atmosphere of 95% air, 5% $CO_2$ at 37° C. Transient transfection (5 μg of test construct and 0.1 or 0.2 μg pCMVβ-gal per plate as a control for transfection efficiency) was performed overnight in 3% FCS/DMEM/F12 using a DNA/$CaPO_4$ co-precipitation method, modified from Ginot et al (Reference 54). Plasmid DNA was isolated by twice banding over a CsCl gradient, followed by extensive dialysis against TE buffer. Hepatocyte response to glucose was evaluated by providing serum-free DMEM/F12 medium (JRH Biosciences, Lenexa, Kans.) custom blended without glucose, to which glucose or L(+)-lactate were subsequently added. To control for osmotic forces, carbohydrate concentration was maintained by substituting equimolar amounts of L(+)-lactate for glucose, up to 10 mM. Reconstituted, defined medium contained amino acids at 20× concentration of rat arterial plasma, dexamethasone $10^{-7}$M (Sigma), PCN/Strep [100 μU/ml PCN, 100 mcg/ml streptomycin](Sigma), human apo-transferrin 0.01 mg/ml (Sigma), and fatty-acid free, bovine serum albumin 1 mg/ml (Boehringer Mannheim Biochemicals, Indianapolis, Ind.). Bovine insulin (GibcoBRL, Gaithersburg, Md.), was added from a sterile filtered, $10^{-4}$M stock, dissolved in 0.1M HCl. D+Glucose was added from a 140 mg/ml sterile filtered stock solution. L(+)-lactate (Sigma) was dissolved into defined medium just before addition to cells. Stable transfection was performed as described (Bonifacino, J. Current Protocols in Molecular Biology, 1997, J. Wiley, and Sons). Briefly, 70% confluent H4IIE cells (a generous gift of Dr. John Koontz, University of Tennessee) were co-transfected with p(GIRE)$_3$BP-12xfur (2 μg/60 mm plate) and pRcCMV/Neo (Invitrogen, Carlsbad, Calif.) (2 μg/60 mm plate), using the adenovirus/polyethylenimine/DNA-conjugate method (References 55). Colonies were isolated under selection in G418 (0.3 mg/ml) (GibcoBRL, Gaithersburg, Md.), and screened for human insulin production by human insulin specific RIA (Linco, Inc) of conditioned medium. An insulin secreting cell line, designated A3, was utilized to document glucose dependent insulin secretion. Two groups of A3 cells expanded to 80% confluence in triplicate wells of collagen coated, 6-well plates were washed twice with PBS to remove traces of serum. Thereafter, cells were alternated between medium containing either 10 mM L(+)-lactate, or 10 mM glucose every two days, for eight days. Culture medium was changed daily. One group was initially provided lactate. The other group initially received glucose. Cells were washed every second day to minimize mechanical stimulation, while reducing carry-over contamination, and conditioned medium was collected just prior to each wash.

Reporter Assays

Luciferase assays were performed using the Luciferase Reporter Assay System (Promega, Madison, Wis.). Twenty microliters of cell lysate, created by adding 250 μl of Reporter Lysis Buffer (Promega, Madison, Wis.) per 60 mm plate, was combined with 100 μl of Luciferase Assay Buffer per well of a 96 well plate. Emitted light was measured for 20 seconds at ambient temperature in a Model ML 3000 plate reading luminometer (Dynatech, Chantilly, Va.). β-galactosidase assays were performed using the same instrument. However, for these assays 10 μl of lysate were combined with 100 μl of Lumigal (Lumigen, Detroit, Mich.), and emitted light measured for 10 seconds at 37° C.

Protein Labeling

Protein labeling using [$^{35}$S]-methionine/cysteine was performed essentially as described by Marriott, et al. (Reference 56). Freshly plated primary hepatocytes were transfected by Ca/$PO_4$ DNA co-precipitation, and cultured overnight in 3% FCS/DMEM/F12 (Mediatech Cellgro). Cells were washed twice in 1×PBS, and provided a methionine/cysteine depleted medium (JRH Biosciences, Lanexa, Kans.) for two hours before addition of 4 mCi of [$^{35}$S]-methionine/cysteine (Promix, Amersham/Pharmacia Biotech, Arlington Heights, Ill.) per 100 mm plate. Cultures were continued for either 4 hours, or overnight, and conditioned medium collected. Cells were washed twice, and collected in 1×PBS, prior to lysis via three cycles of freeze/thaw. Conditioned media and cell lysates were immunoprecipitated with human insulin specific antiserum (Linco Research, St. Charles, Mo.), and Protein-A-Sepharose CL-4B (Pharmacia Biotech). Immune complexes were subjected to denaturing SDS-PAGE using an 18% polyacrylamide separating gel, and a 4% stacking gel. MESNA (2-mercaptoethanesulfonic acid) (0.4M) (Sigma, St. Louis, Mo.) was included in the loading buffer to assure complete reduction of disulfide bonds. A commercial polypeptide standard, which included the bovine insulin B-chain, and [$^{125}$I]-labeled human insulin, mono-iodinated on the A-chain (Linco Research, St. Charles, Mo.), were included as positive controls for the B and A chains, respectively. After drying overnight, gels were exposed for 24 days, and detected using a phosphor-imager (Molecular Dynamics, Sunnyvale, Calif.).

Insulin in conditioned medium was measured using either a dual monoclonal antibody Microparticle Enzyme Immunoassay (MEIa) (IMx Insulin, Abbott Diagnostics, Abbott Park, Ill.), or a standard anti-human insulin RIA kit (Linco Research, St. Charles, Mo.). The manufacturer of the dual monoclonal antibody MEIa reports the dynamic range as 1-300 μU/ml, the sensitivity as greater than 1.0 μU/ml, the cross-reactivity with human proinsulin=0.005%, within assay CV's of 4.0%, between assay coefficient of variation 4.5%, and total run coefficient of variation of 6.0%, at a mean concentration of 8.3 μU/ml. The standard RIA kit is reported to have cross-reactivities of human proinsulin<0.2%, Des 31,32 insulin<0.2%, Des 64,65 insulin=76%, rat insulin<1.0%. Each was used according to manufacturers' instructions.

Northern Analysis

Ten micrograms of total RNA per lane, isolated from transduced primary hepatocytes using TRIzol Reagent (Gibco-BRL/Life Technologies, Gaithersberg, Md.), was electrophoresed on a 1%-agarose-7% formaldehyde gel. Following capillary transfer and UV cross-linking to a nylon membrane (Hybond-N, Amersham/Pharmacia Biotech, Arlington Heights, Ill.), blots were pre-hybridized, and hybridized at 68° C. using QuikHyb (Stratagene, La Jolla, Calif.), and washed for 30 minutes at 68° C. with a 0.1%-SSC/0.1% SDS-solution. Images were developed, and quantified using a phosphor-imager with accompanying densitometry software (Molecular Dynamics, Sunnyvale, Calif.). Following initial analysis using a human insulin probe, membranes were stripped and re-probed using a human GAPDH sequence. Probes were labeled using random priming (Prime-It II, Stratagene, La Jolla, Calif.) of plasmid restriction fragments derived from either pLinklfurIIfur for insulin, or pBSh-GAPDH for GAPDH (a kind gift from Dr. Maria Alexander-Bridges, Howard Hughes Medical Institute, Massachusetts General Hospital, Boston, Mass.).

Human Insulin, Rat C-Peptide RIA

Concentrations of human insulin in conditioned medium, or rat serum, were determined using a human insulin specific RIA reported to have less than 0.1% cross-reactivity with rat insulin, <0.02% cross-reactivity with human proinsulin, and human des 31,32 split-insulin. Cross-reactivity to human des 64,65 split-insulin is reported to be 76% (Linco Research, St. Charles, Mo.). Rat C-peptide was measured using an RIA with less than 1% cross reactivity to human C-peptide, human insulin, or human proinsulin (Linco Research, St. Charles, Mo.).

RT-PCR

Immediately upon sacrifice livers of treated and control animals were flash-frozen in liquid nitrogen, and stored at −70° C. Total RNA (5 µg), obtained by using Trizol (Gibco BRL, Gaithersburg, Md.) per manufacturer's instructions, was subjected to reverse transcription using an oligo-dT$_{17}$ primer, recombinant RNAsin, and Moloney-Murine Leukemia Virus Reverse Transcriptase (M-MLV RT) (all Promega, Madison, Wis.). M-MLV RT was inactivated at 95° C., and PCR reactions were performed using a Gene Amp PCR System 9600 thermal cycler (Perkin Elmer, Norwalk, Conn.), and AmpliTaq DNA Polymerase (Perkin Elmer, Norwalk, Conn.). The cDNA-mixture was allowed to react for 19 (GAPDH), or 22 (insulin) cycles. Primers used for human insulin were 5'-ACCATGGCCCTGTGGATGCGC-3' (SEQ ID No.: 11) (forward), and 5'-CTAGTTGC-AGTAGTTCTC-CAG-3" (SEQ ID No.: 12) (reverse). Primers for GAPDH were 5'-CTGGTCATCAATGGGA-AAC-3' (SEQ ID No.: 13) (forward), and 5'-CAAAGTTGTCATGG-ATGACC-3' (SEQ ID No.: 14) (reverse).

Animals Studies

All studies were performed on male Sprague-Dawley rats, 200-300 gm, housed in individual cages, and exposed to twelve-hour cycles of light and dark. All procedures were approved by the Institutional Animal Care and Use Committees of Emory University, and the Atlanta VA Medical Center. Unless otherwise specified, animals were provided water and standard rodent chow ad libitum.

Animals were made diabetic by intravenous administration of streptozotocin (STZ) (Pfanstiehl Laboratories, Inc., Waukegan, Ill.), dissolved in citrate buffer, pH 4.0. The diagnosis of diabetes mellitus was based upon findings of two or more consecutive random blood glucose values greater than 250 mg/dl, and ketonuria greater than, or equal to, 3 (out of 5 possible) by urine test strip. Blood glucose was measured via the glucose oxidase method, using tail-blood and a One-Touch Profile portable blood glucose monitor (Lifescan, Inc., Milpitas, Calif.). Urine pH, bilirubin, and acetoacetate were assessed using Chemstix 10 (Boehringer Mannheim, Elkhart, Id.). Upon diagnosis of diabetes treatment with subcutaneous injections of insulin (U-100 Lente recombinant human insulin, Lilly Co., Indianapolis, Ind., or U-40 PZI beef/pork insulin, Blue Ridge Pharmaceuticals, Greensboro, N.C.) was initiated.

On the second day following STZ injection, animals underwent recovery surgery for portal system injections of Ad/(GIRE)$_3$BP-1 2xfur, or sham treatment with either Ad dl312, or carrier alone (0.9% NaCl). Surgical anesthesia was achieved using intraperitoneal ketamine 10 mg/xylazine 1 mg/100 gm body-weight. Ad/(GIRE)$_3$BP-1 2xfur-treated animals received $3.6 \times 10^8$–$3.6 \times 10^9$ PFU, Ad dl312-treated animals an equivalent Addl312 dose determined by measurement of OD$_{260}$ while NaCl-treated animals received injections of equivalent volume (Reference 57). The insulin injections begun upon diagnosis of diabetes mellitus were continued for from 1 to 6 days following surgery, or until signs of endogenous insulin production (accelerated weight gain, sustained elevation in urine pH and resolution of ketosis, or a tendency for hypoglycemia) became apparent. Animals were monitored daily to every third day for changes in weight, blood glucose, and urine chemistries. Serum for insulin RIA was obtained via jugular venipuncture under Metofane (Mallinckrodt Veterinary, Inc., Mundelein, Ill.) induced inhalation anesthesia, and was aliquoted and stored at −20° C. prior to assay.

Statistics

Means and standard errors of the mean were calculated using programs resident in either Sigma Plot v.3.2, or Excel 97. P values were calculated using a one-tailed t-test, assuming unequal variances.

From the above, it is concluded that the invention of this application is a successful application of hepatic insulin gene therapy in two distinct rodent models of diabetes mellitus. Utilizing our chimeric glucose and insulin responsive promoter transcriptional regulation of transgenic insulin significantly improves both STZ-induced hyperglycemia, and the spontaneous hyperglycemia in DP BB Wor rats without producing lethal hypoglycemia. Additional work is contemplated to avoid unacceptably broad glucose excursion, and to develop a vector delivery system capable of allowing sustained transgene function. This may ultimately allow the extension of insulin gene therapy studies to humans.

The present invention also includes therapeutic or pharmaceutical compositions comprising a derivative of the construct of the invention in a form which can be combined with or in combination with a pharmaceutically acceptable carrier for any appropriate manner for administration, including, for example, oral, nasal, intravenous or intramuscular administration. Appropriate dosages, duration and frequency of administration would be determined by known factors, such as the condition of the patient, the type and severity of the disease and the method of administration. The term "carrier" includes a diluent, adjuvant, excipient, or vehicle with which the peptide is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic compositions, if desired, can also contain minor amounts of wetting or emulsifying agents, or pH buffering agents. These compositions can take the form of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

The composition may be formulated in accordance with routine procedures as a pharmaceutical composition adapted for local, or systemic injection or administration to human beings. Typically, compositions for local or systemic injection administration are solutions in sterile isotonic aqueous buffer. Where necessary, the composition may also include a solubilizing agent and a local anesthetic, such as lidocaine to ease pain at the site of the injection. Generally, the ingredients are supplied either separately or mixed together in unit dosage form, for example, as a dry lyophilized powder or water free concentrate in a hermetically sealed container, such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts, include those formed with free amino groups, such as those derived from hydrochloric, phosphoric, acetic, oxalic, tartaric acids, etc., and those formed with free carboxyl groups, such as those derived from sodium, potassium, ammonium, calcium, ferric hydroxides, isopropylamine, triethylamine, 2-ethylamino ethanol, histidine, procaine, etc.

The present invention also provides for the modification of the derivatives of the construct of the invention such that it is more stable once administered to a subject, i.e., once administered it has a longer time period of effectiveness as compared to unmodified peptide. Such modifications are well known to those of skill in the art, e.g., polyethylene glycol derivatization (PEGylation), microencapsulation, etc.

While this invention has been described as having preferred sequences, ranges, steps, materials, or designs, it is understood that it includes further modifications, variations, uses and/or adaptations thereof following in general the principle of the invention, and including such departures from the present disclosure as those come within the known or customary practice in the art to which the invention pertains, and as may be applied to the central features hereinbeforesetforth, and fall within the scope of the invention and of the limits of the appended claims. It is further understood that the present invention is not limited to the claims appended hereto.

REFERENCES

1. Eisenbarth G S. Type I diabetes mellitus: *A chronic autoimmune disease*. N Engl J Med 1986; 314:1360-1368.
2. Falqui L, Martinenghi S, Severini G M, et al. *Reversal of diabetes in mice by implantation of human fibroblasts genetically engineered to release mature human insulin*. Human Gene Therapy 1999; 10:1753-1762.
3. Muzzin P, Eisensmith R C, Copeland K G, Woo S L C. *Hepatic insulin gene expression as treatment for Type 1 diabetes mellitus in rats*. Mol Endo 1997; 11:833-837.
4. Gros L, Riu E, Montoliu L, Ontiveros M, Lebrigand L, Bosch F. *Insulin production by engineered muscle cells*. Human Gene Therapy 1999; 10:1207-1217.
5. Short D K, Okada S, Yamauchi K, Pessin J E. *Adenovirus-mediated transfer of a modified human proinsulin gene reverses hyperglycemia in diabetic mice*. American Journal of Physiology 1998; 275:E748-E756.
6. Rivera V M, Wang W, Wardwell S, et al. *Regulation of protein secretion through controlled aggregation in the endoplasmic reticulum*. Science 2000; 287:826-830.
7. Selden R F, Skoskiewicz M J, Russell P S, Goodman H M. *Regulation of insulin-gene expression*. N Engl J Med 1987; 317:1067-1076.
8. Kolodka T M, Finegold M, Moss L, Woo S L C. *Gene therapy for diabetes mellitus in rats by hepatic expression of insulin*. Proc Natl Acad Sci USA 1995; 92:3293-3297.
9. Tuch B E, Tabiin M T, Casamento F M, Simpson A M, Marshall G M. *Transplantation of genetically engineered insulin-producing hepatocytes into immunoincompetent mice*. Transplantation Proceedings 1998; 30:473.
10. Valera A, Fillat C, Costa C, et al. *Regulated expression of human insulin in the liver of transgenic mice corrects diabetic alterations*. FASEB J 1994; 8:440-447.
11. Kaneda Y, Iwai K, Uchida T. *Introduction and expression of the human insulin gene in adult rat liver*. Journal of Biological Chemistry 1989; 264:12126-12129.
12. Yamaguchi M, Kuzume M, Matusumoto T, et al. *Insulin gene transfer compensates pancreatic b-cell function in diabetic rats*. Transplantation Proceedings 1998; 30:2913.
13. Sugiyama A, Hattori S, Tanaka S, et al. *Defective adenoassociated viral-mediated transfection of insulin gene by direct injection into liver parenchyma decreases blood glucose of diabetic mice*. Hormone and Metabolic Research 1997; 29:599-603.
14. Abai A, Hobart P, Barnhart K M. *Insulin Delivery with Plasmid DNA*. Human Gene Therapy 1999; 10:2637-2649.
15. Lu D, Tamemoto H, Shibata H, Saito I, Takeuchi T. *Regulatable production of insulin from primary-cultured hepatocytes: insulin production is up-regulated by glucagon and cAMP and down-regulated by insulin*. Gene Therapy 1998; 5:888-895.
16. Gros L, Montoliu L, Riu E, Lebrigand L, Bosch F. *Regulated production of mature insulin by non-b-cells*. Human Gene Therapy 1997; 8:2249-2259.
17. Wanke I E, Wong N C. *Specific problems facing gene therapy for insulin-dependent diabetes mellitus: glucose-regulated insulin secretion from hepatocytes*. Proceeding of the Western Pharmacology Society 1997; 40:131-133.

18. Simpson A M, Marshall G M, Tuch B E, et al. *Gene therapy of diabetes: glucose-stimulated insulin secretion in a human hepatoma cell line (HEP G2ins/g)*. Gene Therapy 1997; 4:1202-1215.
19. Powell D R, Suwanichkul A, Cubbage M, Lee P D K. *Regulation of insulin-like growth factor binding protein-1 (IGFBP-1) protein levels, mRNA levels and promoter activity by insulin (IN) and IGF-1 in HepG2*. Endo Society 1990:280A.
20. Powell D R, Suwanichkul A, Cubbage M L, DePaolis L A, Snuggs M B, Lee P D K. *Insulin inhibits transcription of the human gene for insulin-like growth factor-binding protein-1*. Journal of Biological Chemistry 1991; 266:18868-18876.
21. Powell D R, Suwanichkul A. *HNF1 activates transcription of the human gene for insulin-like growth factor binding protein-1*. DNA and Cell Biology 1993; 12:283-289.
22. Suwanichkul A, Cubbage M L, Powell D R. *The promoter of the human gene for insulin-like growth factor binding protein-1. Basal promoter activity in HEP G2 cells depends upon liver factor B1*. Journal of Biological Chemistry 1990; 265:21185-21193.
23. Suwanichkul A, DePaolis L A, Lee P D K, Powell D R. *Identification of a promoter element which participates in cAMP-stimulated expression of human insulin-like growth factor-binding protein-1*. Journal of Biological Chemistry 1993; 268:9730-9736.
24. Suwanichkul A, Morris S L, Powell D R. *Identification of an insulin-responsive element in the promoter of the human gene for insulin-like growth factor binding protein-1*. Journal of Biological Chemistry 1993; 268:17063-17068.
25. Suwanichkul A, Allander S V, Morris S L, Powell D R. *Glucocorticoids and insulin regulate expression of the human gene for insulin-like growth factor-binding protein-1 through proximal promoter elements*. Journal of Biological Chemistry 1994; 269:30835-30841.
26. Hughes S D, Johnson J H, Quaade C, Newgard C B. *Engineering of glucose-stimulated insulin secretion and biosynthesis in non-islet cells*. 1992; 89:688-692.
27. Rencurel F, Waever G, Antoine B, et al. *Requirement of glucose metabolism for regulation of glucose transporter type 2 (GLUT 2) gene expression in liver*. Biochemical Journal 1996; 314:903-909.
28. Villafuerte B C, Goldstein S, Murphy L J, Phillips L S. *Nutrition and Somatomedin XXV. Regulation of insulin-like growth factor binding protein-1 in primary cultures of normal rat hepatocytes*. Diabetes 1991; 40:837-841.
29. Ooi G T, Tseng L Y-H, Tran M Q, Rechler M M. *Insulin rapidly decreases insulin-like growth factor-binding protein-1 gene transcription in streptozotocin-diabetic rats*. Molecular Endocrinology 1992; 6:2219-2228.
30. Pao C-I, Farmer P K, Begovic S, Goldstein S, Wu G-J, Phillips L S. *Expression of hepatic insulin-like growth factor-I and insulin-like growth factor-binding protein-1 genes is transcriptionally regulated in streptozotocin-diabetic rats*. Molecular Endocrinology 1992; 6:969-977.
31. Suh D-S, Zhou Y, Ooi G T, Rechler M M. *Dexamethasone stimulation of rat insulin-like growth factor binding protein-1 (IGFBP-1) promoter activity involves the interaction of multiple transcription factors*. Progress in Growth Factor Research 1995; 6:131-140.
32. Cuif M-H, Cognet M, Boquet D, Tremp G, Kahn A, Vaulont S. *Elements responsible for hormonal control and tissue specificity of L-type pyruvate kinase gene expression in transgenic mice*. Molecular and Cellular Biology 1992; 12:4852-4861.
33. Cognet M, Lone Y C, Vaulont S, Kahn A, Marie J. *Structure of the rat L-type pyruvate kinase gene*. J Mol Biol 1987; 196:11-25.
34. Bergot M-O, Diaz-Guerra M-J M, Puzenat N, Raymondjean M, Kahn A. *Cis-regulation of the L-type pyruvate kinase gene promoter by glucose, insulin and cyclic AMP*. Nucleic Acids Research 1992; 20:1871-1878.
35. Vaulont S, Munnich A, Decauz J-F, Kahn A. *Transcriptional and post-transcriptional regulation of L-type pyruvate kinase gene expression in rat liver*. Journal of Biological Chemistry 1986; 261:7621-7625.
36. Goswami R, Lacson R, Unterman T. *Identification of insulin and glucocorticoid response sequences in the rat IGF binding protein-1 (IGFBP-1) promoter*. Endocrine Society 1993; 1915B:529.
37. Shu D-S, Ooi G T, Lesniak M A S. *Inhibition of IGFBP-1 gene expression by insulin and stimulation by dexamethasone, cyclic amp, and phorbol esters are mediated by different cis-acting elements in the rat IGFBP-1 promoter*. Endocrine Society 1993; 1916B:529.
38. Bergot M-O, Diaz-Guerra M-J M, Puzenat N, Raymondjean M, Kahn A. *Cis-regulation of the L-type pyruvate kinase gene promoter by glucose, insulin and cyclic AMP*. Nucleic Acids Res 1992; 20:1871-1878.
39. Smeekens S P, Chan S J, Steiner D F. *The biosynthesis and processing of neuroendocrine peptides: identification of proprotein convertases involved in intravesicular processing*. Progress in Brain Research 1992; 92:235-246.
40. Groskreutz D J, Sliwkowski M X, Gorman C M. *Genetically engineered proinsulin constitutively processed and secreted as mature, active insulin*. Journal of Biological Chemistry 1994; 269:6241-6245.
41. Steiner D F, Smeekens S P, Ohag S, Chan S J. *The New Enzymology of Precursor Processing Endoproteases*. Journal of Biological Chemistry 1992; 267:23435-23438.
42. Simonson G D, Groskreutz D J, Gorman C M, MacDonald M J. *Synthesis and processing of genetically modified human proinsulin by rat myoblast primary cultures*. Human Gene Therapy 1996; 7:71-78.
43. Unger R H, Foster D W. Chapter 21. In: Wilson J D, Foster D W, Kronenberg H M, Williams R H, eds. *Williams Textbook of Endocrinology*. Vol. 9th. Philadelphia, London, Toronto, Montreal, Sydney: W.B Saunders Co., 1998:973-1059.
44. Robertson D G, Marino E M, Thule P M, Seneviratne C K, Murphy L J. *Insulin and glucocorticoids regulate IGFBP-1 expression via a common promoter region*. Biochemical Biophysical Research Communication 1994; 200:226-232.
45. Goswami R, Lacson R, Yang E, Sam R, Unterman T. *Functional analysis of glucocorticoid and insulin response sequences in the rat insulin-like growth factor-binding protein-1 promoter*. Endocrinology 1994; 134:736-743.
46. Suh D S, Ooi G T, Rechler M M. *Identification of cis-elements mediating the stimulation of rat insulin-like growth factor-binding protein-1 promoter activity by dexamethasone, cyclic adenosine 3',5'-monophosphate, and phorbol esters, and inhibition by insulin*. Molecular Endocrinology 1994; 8:794-805.
47. Goldstein S, Sertich G, Levan K R, Phillips L S. *Nutrition and somatomedin. XIX. Molecular regulation of insulin-like growth factor-I in streptozotocin-diabetic rats*. Molecular Endocrinology 1988; 2:1093-1100.
48. Minematsu S, Watanabe M, Tsuchiya N, Amagaya S. *Diurnal variations in blood chemical items in Sprague-Dawley rats*. Experimental Animals 1995; 44:223-232.

49. Haughton C L, Dillehay D L, Phillips L S. *Insulin replacement therapy for the rat model of streptozotocin-induced diabetes mellitus*. Laboratory Animal Science 1999; 49:639-44.
50. Koopmans S J, Sips H C M, Krans H M J, Radder J K. *Pulsatile intravenous insulin replacement in streptozotocin-diabetic rats is more efficient than continuous delivery: effects on glycemic control, insulin-mediated glucose metabolism and lipolysis*. Diabetologia 1996; 39:391-400.
51. Wang R N, Bouwens L, Kloeppel G. *Beta-cell proliferation in normal and streptozotocin-treated newborn rats: site, dynamics and capacity*. Diabetologia 1994; 37:1088-1096.
52. Like A A, Guberski D L, Butler L. *Influence of Environmental Viral Agents on Frequency and Tempo of Diabetes Mellitus in BB/Wor Rats*. Diabetes 1991; 40:259-262.
53. Seglen P O. Preparation of rat liver cells. III. *Enzymatic requirements for tissue dispersion*. Exp Cell Res 1973; 82:391-398.
54. Ginot F, Decaux J-F, Cognet M, et al. *Transfection of hepatic genes into adult rat hepatocytes in primary culture and their tissue-specific expression*. Eur J Biochem 1989; 180:289-294.
55. Baker A, Saltik M, Lehrmann H, et al. *Polyethylenimine (PEI) is a simple, inexpensive and effective reagent for condensing and linking plasmid DNA to adenovirus for gene delivery*. Gene Therapy 1997; 4:773-782.
56. Marriott D, Gillece-Castro B, Gorman C M. *Prohormone convertase-1 will process prorelaxin, a member of the insulin family of hormones*. Molecular Endocrinology 1992; 6:1441-1450.
57. Mittereder N, March K L, Trapnell B C. *Evaluation of the concentration and bioactivity of adenovirus vectors for gene therapy*. Journal of Virology 1996; 70:7498-7509.

What I claim is:

1. An insulin regulator construct, comprising:
   a) a nucleotide sequence set forth in one of SEQ ID NO.: 3, SEQ ID NO.: 4, SEQ ID NO.: 5, and SEQ ID NO.: 6; and
   b) a sequence encoding insulin or proinsulin operably linked to the promoter element of said construct.

2. The insulin regulator construct of claim 1, wherein the nucleotide sequence comprises:
   a) a glucose response element (GIRE) of a liver-pyruvate (L-PK) gene promoter; and
   b) an insulin-sensitive element of an insulin-like growth factor binding protein-1 (IGFBP-1) basal promoter.

3. The insulin regulator construct of claim 2, wherein: said glucose response element comprises a hepatic nuclear factor-4 (HNF-4) binding site and a glucose responsive site.

4. The insulin regulator construct of claim 3, further comprising:
   a plurality of said glucose response elements.

5. The insulin regulator construct of claim 3, wherein: the sequence of said HNF-4 binding site and said glucose responsive site is in a native orientation.

6. The insulin regulator construct of claim 3, wherein: the sequence of said HNF-4 binding site and said glucose responsive site is reversed from a native orientation.

7. The insulin regulator construct of claim 2, wherein: said glucose response element is inserted upstream of said insulin-sensitive element in an insulin-like growth factor binding protein-1 (IGFBP-1) basal promoter.

8. The insulin regulator construct of claim 2, wherein: said glucose response element comprises a nucleotide sequence set forth in SEQ ID NO.: 1.

9. The insulin regulator construct of claim 2, wherein: said insulin-sensitive element comprises a nucleotide sequence set forth in SEQ ID NO.: 2.

10. The insulin regulator construct of claim 1, which is not stimulated by exposure to lactate or fructose.

11. The insulin regulator construct of claim 1, which is stimulated by exposure to glucose and inhibited by exposure to insulin.

12. A vector comprising the construct of claim 1.

13. An adenoviral vector comprising the construct of claim 1.

14. The construct of claim 1, wherein said construct comprises a transgene.

15. A pharmaceutical composition comprising the construct of claim 1 and a pharmaceutically acceptable carrier or diluent.

16. A method of treating diabetic conditions in a subject by administering an effective amount of the construct of claim 1.

17. A method of regulating insulin production in a subject by administering an effective amount of the construct of claim 1.

18. A method of modulating hyperglycemia, while avoiding severe hypoglycemia, in a subject by administering an effective amount of the construct of claim 1.

19. A method of increasing fat catabolism in a subject by administering an effective amount of the construct of claim 1.

20. A method of reducing protein catabolism in a subject by administering an effective amount of the construct of claim 1.

* * * * *